United States Patent
Peng et al.

(10) Patent No.: US 7,196,230 B2
(45) Date of Patent: Mar. 27, 2007

(54) PHOSOXOPHITE LIGANDS AND USE THEREOF IN CARBONYLATION PROCESSES

(75) Inventors: Wei-Jun Peng, Hurricane, WV (US); David Robert Bryant, Charleston, WV (US)

(73) Assignee: Union Carbide Chemicals & Plastics Technology Corporation, Danbury, CT (US)

(*) Notice: Subject to any disclaimer, the term of this patent is extended or adjusted under 35 U.S.C. 154(b) by 318 days.

(21) Appl. No.: 10/504,247

(22) PCT Filed: Mar. 4, 2003

(86) PCT No.: PCT/US03/06456

§ 371 (c)(1), (2), (4) Date: Aug. 10, 2004

(87) PCT Pub. No.: WO03/078444

PCT Pub. Date: Sep. 25, 2003

(65) Prior Publication Data

US 2006/0100453 A1     May 11, 2006

Related U.S. Application Data

(60) Provisional application No. 60/363,725, filed on Mar. 11, 2002.

(51) Int. Cl.
*C07F 9/02* (2006.01)
(52) U.S. Cl. .......................... 568/451; 558/78; 558/77; 556/13; 556/404; 568/429; 568/454
(58) Field of Classification Search .................... 556/9, 556/13, 404; 558/78, 77; 568/429
See application file for complete search history.

(56) References Cited

U.S. PATENT DOCUMENTS

| | | |
|---|---|---|
| 3,527,809 A | 9/1970 | Pruett et al. |
| 4,148,830 A | 4/1979 | Pruett et al. |
| 4,247,486 A | 1/1981 | Brewester et al. |
| 4,599,206 A | 7/1986 | Billig et al. |
| 4,748,261 A | 5/1988 | Billig et al. |
| 4,755,625 A | 7/1988 | Maerkl et al. |
| 5,874,641 A | 2/1999 | Burke et al. |
| 5,929,289 A | 7/1999 | Abatjoglou et al. |
| 6,156,936 A | 12/2000 | Drent et al. |
| 6,570,033 B2 * | 5/2003 | Rottger et al. ................ 558/78 |

FOREIGN PATENT DOCUMENTS

| | | |
|---|---|---|
| DE | 19602301 A | 7/1996 |
| EP | A1-213639 | 3/1987 |
| EP | A1-353770 | 2/1990 |
| EP | A1-569328 | 11/1993 |
| EP | A1-1008581 | 6/2000 |
| EP | A1-1099677 | 5/2001 |
| EP | A1-1099678 | 5/2001 |
| EP | A1-1201675 | 5/2002 |
| JP | 9-87292 | 3/1997 |
| WO | WO 1995/14659 | 6/1995 |
| WO | WO 2000/09467 | 2/2000 |
| WO | WO 2001/58589 | 8/2001 |
| WO | WO 2001/85739 | 11/2001 |
| WO | WO 2002/00670 | 1/2002 |
| WO | WO 2003/016320 | 2/2003 |
| WO | WO 2003/078444 | 9/2003 |
| WO | WO 2004/035595 | 4/2004 |

OTHER PUBLICATIONS

Selent et al., New Phosphorus Ligands for the Rhodium-Catalyzed Isomerization/Hydroformylation of Internal Octenes, Angew. Chem. Int. Ed. 2001, 40, 1696-1698.*
Chemical Abstracts No. 125:33742 (1996).
Chemical Abstracts No. 124:56087 (1995).
Chemical Abstracts No. 118:102081 (1993).
C. Botteghi et al., Journal of Molecular Catalysis, A, Chemical, 1999, 143, pp. 311-323.
D. Selent, et al., Angewandte Chemie, Intl. Edition, 2001, 40 (9), pp. 1696-1698.
S. D. Pastor et al., Inorganic Chemistry, 1996, 35 (4), 949-958.
Peng, Wei-Jun, "Bis-chelating Ligand and Use Thereof in Carbonylation Processes," Co-pending U.S. Appl. No. 10/527,568, filing date Mar. 11, 2005.

* cited by examiner

*Primary Examiner*—Thurman Page
*Assistant Examiner*—Chukwuma Nwaonicha
(74) *Attorney, Agent, or Firm*—Marie F. Zuckerman

(57) ABSTRACT

A novel organophosphorus composition and synthesis thereof, the composition being characterized by one phosphite moiety, one phosoxophite moiety, and a plurality of sterically bulky substituents. The novel composition finds utility as a ligand in Group VIII transition metal phosoxophite complex catalysts and complex catalyst precursors that are used in carbonylation processes, preferably, hydroformylation processes. Additionally, there is disclosed a novel method of preparing a phosphoromonochloridite composition that finds utility as a precursor to the novel phosoxophite composition.

40 Claims, No Drawings

PHOSOXOPHITE LIGANDS AND USE THEREOF IN CARBONYLATION PROCESSES

This application is a 371 of PCT/US03/06456 filed Mar. 4, 2003 which claims benefit of Ser. No. 60/363,725 filed Mar. 11, 2002.

BACKGROUND OF THE INVENTION

This invention relates to a novel organophosphorus composition, its method of preparation, and its use in transition metal complex catalyzed reactions. Preferably, this invention relates to a novel organophosphorus composition and its use in transition metal phosphorus ligand complex catalyzed carbonylation processes, preferably, hydroformylation processes.

Carbonylation processes directed to the production of oxygenated products are well known and generally involve reaction of an organic compound with carbon monoxide and often a third reactant, preferably, hydrogen. See, for example, J. Falbe, "New Syntheses With Carbon Monoxide," Springer Verlag, New York, 1980. Such processes may include the carbonylation of organic compounds, such as olefins, acetylenes, alcohols, and activated chlorides, with carbon monoxide, and optionally, either hydrogen, alcohol, amine, or water, as well as ring closure reactions of functionally unsaturated compounds, e.g., unsaturated amides, with carbon monoxide. One major class of known carbonylation processes comprises the hydroformylation of an olefinic compound with carbon monoxide and hydrogen to produce oxygenated products, such as aldehydes, followed by reduction, if desired, of the aldehyde to alcohol; or reductive amination of the aldehyde to amine; or oxidation of the aldehyde to carboxylic acid; or aldolization of the aldehyde followed by oxidation to hydroxyacid. Amines and oxygenated products, such as alcohols, carboxylic acids, and hydroxyacids find utility in a multitude of applications, including as solvents, surfactants, monomers for the preparation of polymers, and as intermediates in the synthesis of pharmaceuticals and other industrial chemicals.

Carbonylation processes are known to be facilitated by metal-ligand complex catalysts, particularly Group VIII transition metal-phosphorus ligand complex catalysts. Representative art disclosing a variety of hydroformylation catalysts of various triorganophosphine, triorganophosphite, diorganophosphite, and bisphosphite ligands, is found in the following references: U.S. Pat. No. 3,527,809; U.S. Pat. No. 4,599,206; U.S. Pat. No. 4,748,261; and WO-A1-02/00670. Disadvantageously, many of the transition metal-phosphorus ligand complexes disclosed for carbonylation processes exhibit only moderate or low activity for internal olefins and undesirable isomerization of long chain alpha-olefins to internal olefins. Additionally, the ligands disclosed in the art cannot be easily fine-tuned to provide a high selectivity to the desired hydroformylation product.

More recently, D. Selent et al. disclosed in *Angewandte Chemie Int. Ed.*, 2001, 40, No. 9., 1696–1698, that unsymmetrical bidentate phosphorus ligands of formula I, shown hereinbelow, are useful in the hydroformylation of internal olefins.

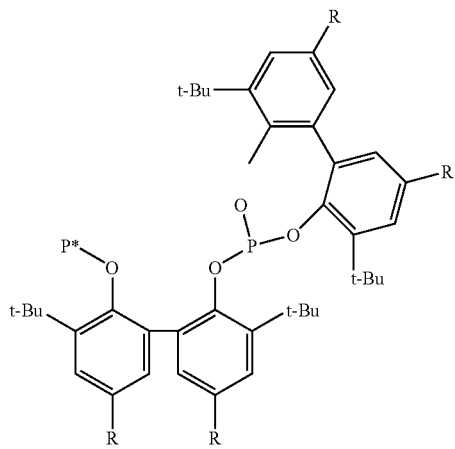

In formula I, each "t-Bu" represents a tertiary butyl moiety; each R is the same and is either a tertiary butyl or methoxy (—OCH$_3$) substituent; and P* is a phosphorus-containing moiety selected from one of the following three formulas:

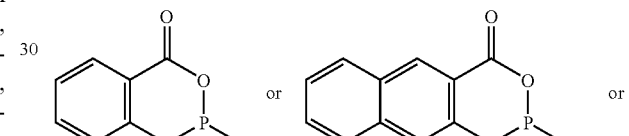

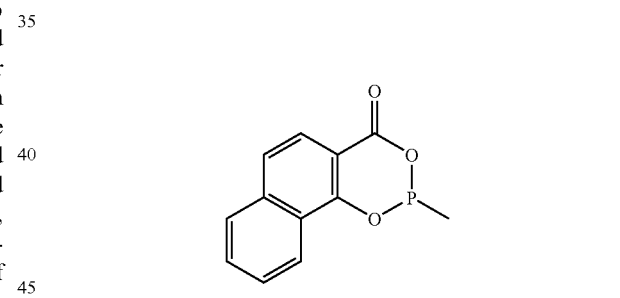

Although these prior art ligands are sufficiently active for hydroformylation of terminal and internal olefins, they achieve an unacceptably low normal (N) to iso (I) products selectivity, as measured by an N:I molar ratio typically of only 2/1 to 4/1, when normal aldehydes are the desired products. With such a low N:I selectivity, the yield of the desired normal product is also unacceptably low, at less than about 75 mole percent, when either internal or terminal olefins are used as substrates. These prior art ligands also lack isomerization selectivity when 3-penten-1-ol is used as a substrate, producing 6-hydroxyhexanal in less than about 70 mole percent yield. 6-Hydroxyhexanal is a precursor to caprolactam, which itself is used in the production of Nylon-6.

In view of the above, a search continues in the art to find novel phosphorus ligands that will provide improved activity, improved isomerization selectivity, improved ease of fine-tuning selectivity, and improved stability in carbonylation processes, preferably, hydroformylation processes.

SUMMARY OF THE INVENTION

In a first aspect, this invention provides for a novel organophosphorus composition selected from the group of compositions represented by generic formulas IIa and IIb hereinbelow:

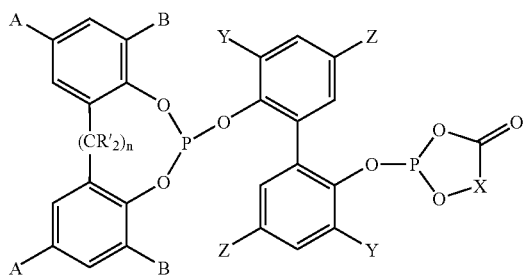

(IIa)

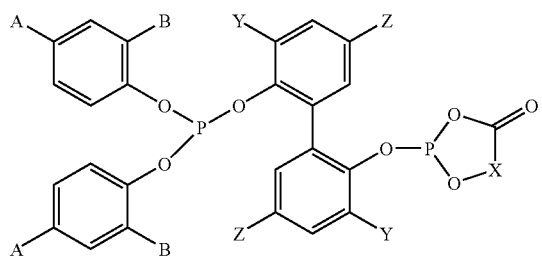

(IIb)

wherein each A and Z is independently selected from the group consisting of hydrogen, halogen, monovalent hydrocarbyl radicals, and tri(hydrocarbyl)silyl radicals; each B and Y is independently selected from aryl radicals, tertiary alkyl radicals, and tri(hydrocarbyl)silyl radicals, with the proviso that at least one B or at least one Y is a tri (hydrocarbyl)silyl radical; each $R^1$ is independently selected from the group consisting of hydrogen, monovalent alkyl radicals and monovalent aryl radicals; n is an integer from 0 to 2; and X is selected from the group consisting of alkyl and aryl diradicals and substituted derivatives thereof. For the purposes of this invention, the segment of formula IIa or IIb having the structure III, shown hereinafter:

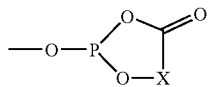

(III)

shall be referred to as a "phosoxophite" moiety, characterized as having a phosphorus atom in a conventional phosphite configuration with one of the oxygen atoms being further bonded to a carbonyl moiety (—C=O). Accordingly, the novel phosphorus compound of this invention shall hereinafter be referred to as a "phosoxophite" composition.

The novel phosoxophite composition of this invention finds utility as a ligand in catalyst and catalyst precursor compositions that are used in carbonylation processes, preferably, hydroformylation processes. Advantageously, the novel phosoxophite composition provides for a carbonylation catalyst of greater activity, improved isomerization selectivity, and improved ease of fine-tuning selectivity, as compared with prior art carbonylation catalysts. In preferred embodiments of this invention, yields of 6-hydroxyhexanal in excess of about 80 mole percent can be achieved in the hydroformylation of 3-penten-1-ol. Moreover, the normal to iso product molar ratio N:I achieved in hydroformylation of either internal or terminal olefins can be significantly improved by use of the novel composition of this invention as a ligand, as compared with prior art ligands. As a further advantage in the hydroformylation of terminal olefins, undesired isomerization of the terminal olefin to internal olefins can also be significantly reduced by use of the novel composition ligand of this invention.

Hereinafter, the description shall specifically describe certain synthetic processes related to formula IIa; but such description shall not be limited specifically thereto. Accordingly, such process conditions described for formula IIa shall be equally and fully applicable to formula IIb, with the exception that the bridging atoms or bond connecting the two phenyl rings having substituents A and B in formula IIa shall be absent in any process application related to formula IIb.

In a second aspect, this invention is a novel synthetic process of preparing the phosoxophite composition of formula IIa comprising contacting a dichloro-bisphosphite composition represented by formula IV:

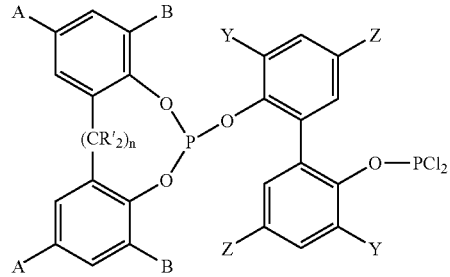

(IV)

wherein A, B, $R^1$, Z, Y, and n are as defined hereinabove in connection with formula IIa, with a hydroxy acid represented by formula V:

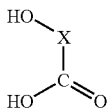

(V)

wherein X is selected, as described hereinbefore, from alkyl and aryl diradicals and substituted derivatives thereof; the contacting of composition IV with composition V being conducted under reaction conditions sufficient to prepare the phosoxophite composition of formula IIa. The aforementioned synthetic process of this invention beneficially and efficiently produces the novel phosoxophite composition IIa, shown hereinbefore. The composition of formula IIb can be prepared in an analogous manner.

In a third aspect, this invention provides for a novel complex catalyst or complex catalyst precursor composition comprising a Group VIII transition metal bonded to at least one molecule of phosoxophite ligand of formula IIa or IIb hereinabove, the transition metal optionally being further bonded to carbon monoxide, hydrogen, or both carbon monoxide and hydrogen. In a fourth and related aspect, this invention provides for a complex catalyst solution or complex catalyst precursor solution comprising a solvent, a complex catalyst or catalyst precursor composition comprising a Group VIII transition metal bonded to at least one phosoxophite ligand, and optionally, free phosoxophite ligand; wherein the bonded and free phosoxophite ligands are represented by formula IIa or IIb hereinabove; and wherein optionally, the Group VIII transition metal may be further bonded to carbon monoxide, hydrogen, or both carbon monoxide and hydrogen. The novel catalyst or catalyst precursor composition and the novel solutions thereof find utility particularly in carbonylation processes, preferably, hydroformylation processes. Unexpectedly, the novel carbonylation catalyst of this invention provides for a more active and more selective carbonylation catalyst, as compared with prior art carbonylation catalysts.

In a fifth aspect, this invention provides for a novel carbonylation process comprising contacting an organic compound capable of being carbonylated with carbon monoxide in the presence of a Group VIII transition metal-phosoxophite ligand complex catalyst, wherein the phosoxophite ligand is represented by formula IIa or IIb hereinabove, the contacting being conducted under carbonylation conditions sufficient to prepare the corresponding carbonylated organic compound. The novel carbonylation process of this invention, including a preferred hydroformylation process of this invention, finds utility in the production of useful organic intermediates, solvents, and monomers. Caprolactam, which is used in the preparation of Nylon-6, is one such useful organic monomer that can be prepared using the carbonylation catalyst and preferred hydroformylation process of this invention.

DETAILED DESCRIPTION OF THE INVENTION

In a primary aspect, the invention described herein pertains to an entirely new class of organophosphorus compositions, hereinafter referred to as "phosoxophite" compositions, which are represented by the following generic formula IIa or IIb hereinafter:

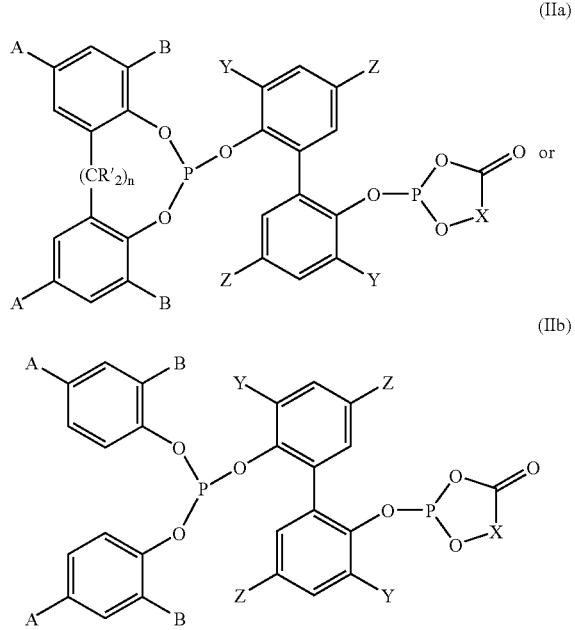

wherein each A and Z is independently selected from the group consisting of hydrogen, halogen, monovalent hydrocarbyl radicals, and tri(hydrocarbyl)silyl radicals; each B and Y is independently selected from aryl radicals, tertiary alkyl radicals, and tri(hydrocarbyl)silyl radicals, with the proviso that at least one B or at least one Y is a tri(hydrocarbyl)silyl radical; X is selected from the group consisting of alkyl and aryl diradicals and substituted derivatives thereof; each $R^1$ is selected from hydrogen, monovalent alkyl and monovalent aryl radicals; and n is an integer from 0 to 2. Preferably, each A and Z is independently selected from the group consisting of hydrogen, halogen, alkyl, aryl, alkaryl, aralkyl, alicyclic, alkoxy, aryloxy, hydrocarbyl carbonyl [—C(O)$R^2$], and hydrocarbyl carboxy [—OC(O)$R^2$] radicals (wherein $R^2$ is a monovalent hydrocarbyl radical), and tri(hydrocarbyl)silyl radicals, the organic, hydrocarbyl and tri(hydrocarbyl)silyl radicals preferably having from 1 to about 20 carbon atoms; more preferably, selected from chloro, bromo, iodo, as well as alkyl, aryl, alkoxy, aryloxy, alicyclic, hydrocarbyl carbonyl, hydrocarbyl carboxy, and tri(hydrocarbyl)silyl radicals, the aforementioned hydrocarbyl and tri(hydrocarbyl)silyl radicals having from 1 to about 20 carbon atoms. Specific illustrative monovalent radicals represented by A and Z include, without limitation, as alkyl radicals: methyl, ethyl, propyl, isopropyl, butyl, sec-butyl, t-butyl, neo-pentyl, sec-amyl, t-amyl, iso-octyl, t-octyl, 2-ethylhexyl, iso-nonyl, iso-decyl, octadecyl, and the like; aryl radicals include phenyl, naphthyl, anthracyl, and the like; aralkyl radicals include benzyl, phenylethyl, and the like; alkaryl radicals include tolyl, xylyl, dimethylphenyls, diethylphenyls, trimethylphenyls, triethylphenyls, p-alkylphenyls, and the like; alicyclic radicals include cyclopentyl, cyclohexyl, cyclooctyl, cyclohexylethyl, 1-methylcyclohexyl, and the like; alkoxy radicals include methoxy, ethoxy, propoxy, butoxys, pentoxys, and the like; aryloxy radicals include phenoxy, naphthoxy, and the like; hydrocarbyl carbonyl radicals include methylcarbonyl, ethylcarbonyl, and the like; hydrocarbyl carboxy radicals include tri(methyl)acetoxy, tri(ethyl) acetoxy, tri(phenyl)acetoxy, and the like; and tri(hydrocarbyl)silyl radicals include tri(methyl)silyl, tri(ethyl)silyl, tri (phenyl)silyl, and the like. Most preferably, each A is independently selected from hydrogen, chloro, bromo, iodo, methyl, ethyl, tertiary butyl, isoamyl, tertiary amyl, tertiary octyl, methoxy, acetyl [CH$_3$C(O)—], propionyl [CH$_3$CH$_2$C (O)—] and trimethylacetoxy [(CH$_3$)$_3$C—C(O)O—] radicals. Most preferably, each Z is independently selected from tertiary butyl, tertiary amyl, tertiary octyl, tri(methyl)silyl, tri(ethyl)silyl, xylyls, dimethylphenyls (more preferably, 2,6-dimethylphenyl), diethylphenyls, trimethylphenyls (more preferably, 2,4,6-trimethylphenyl), and trimethylacetoxy.

The B and Y substituents of formulas IIa and IIb are each independently selected from aryl radicals, tertiary alkyl radicals, and tri(hydrocarbyl)silyl radicals, with the proviso that at least one B or at least one Y is a tri(hydrocarbyl)silyl radical. Preferably, each B and Y is independently selected from tertiary alkyl radicals, aryl and alkaryl radicals not having substituents on the aryl ortho positions, and tri (hydrocarbyl)silyl radicals, the aforementioned radicals having from 3 to about 30 carbon atoms, with the proviso that at least one B or at least one Y is a tri(hydrocarbyl)silyl radical. Suitable examples of tertiary alkyl radicals include, without limitation, tertiary butyl, t-amyl, t-octyl, and the like; aryl radicals include phenyl, naphthyl, anthracyl, and the like; alkaryl radicals include tolyl, xylyl, diethylphenyls, trimethylphenyls, triethylphenyls, p-alkylphenyls, and the like; and tri(hydrocarbyl)silyl radicals include trimethylsilyl, triethylsilyl, triphenylsilyl, triisopropylsilyl, and the like. More preferably, each B is independently selected from tertiary butyl, trimethylsilyl, phenyl, dimethylphenyls (preferably, 3,5-dimethylphenyl), and trimethylphenyls (preferably, 3,4,5-trimethylphenyl radicals, consistent with the proviso mentioned. More preferably, each Y is independently selected from tertiary butyl and trimethylsilyl radicals, consistent with the proviso mentioned. As a preferred proviso, preferably, at least two of the combined B's and Y's are tri(hydrocarbyl)silyl radicals. As a more preferred proviso, both B's are tri(hydrocarbyl)silyl radicals or both Y's are tri(hydrocarbyl)silyl radicals.

Optionally, any of the aforementioned radicals associated with A, B, Y, and Z may be substituted, the word "substituted" to include any substituent, i.e., halo, nitro, amino, cyano, trifluoromethyl, hydroxy, sulfonyl, sulfinyl, and any class of organic substituent (for example, alkyl, aryl, alkoxy, amido, acyl, carbonyloxy, oxycarbonyl, tri(hydrocarbyl)silyl, ether, phosphonyl, and thionyl) that is non-interfering with the formula or its catalytic and stabilizing properties.

Further to the formulas, X may be any alkyl or aryl diradical that can form a ring system in the phosoxophite fragment shown in III and formulas IIa and IIb. Typically, X comprises any aryl diradical having two adjacent binding sites (e.g., 1,2-aryl or 2,3-aryl, etc.), such that a 6-membered phosoxophite ring is formed. Alternatively, X can be an alkyl diradical of from 1 to about 3 carbon atoms (exclusive of the carbon atoms in subsidiary substituents, which may number from 1 to about 20 carbon atoms), such that a 5, 6, or 7-membered ring is formed. Subsidiary substituents include, for example, halo, nitro, cyano, alkoxy, $C_{1-20}$ alkyl groups, and —C(O)R³ wherein R³ is hydrogen or a $C_{1-20}$ alkyl group, so long as the substituent does not interfere with the desired properties of the phosoxophite composition. Illustrative alkyl and aryl diradicals represented by X include without limitation methylene (—CH₂—), ethylene (—CH₂CH₂—), 1,3-propylene (—CH₂CH₂CH₂—), 1,2-phenylene (—C₆H₄—), 1,2-naphthylene (—C₁₀H₆—), 2,3-naphthylene (—C₁₀H₆), 3,5-dichloro-1,2-phenylene, 3,5-dibromo-1,2-phenylene, 3-iodo-5-methyl-1,2-phenylene, 3,5-diisopropyl-1,2-phenylene, 3,5,6-trichloro-1,2-phenylene, 3-phenyl-1,2-phenylene, 1,1-diethyl-1,1-methylene, 1,1-cyclohexylidene, 1,1-cycloheptylidene, 3-isopropyl-6-methyl-1,2-phenylene, and the like. More preferably, X is selected from 1,1-alkyl, 1,2-alkyl, 1,2-phenylene, 1,2-naphthylene, and 2,3-naphthylene diradicals, and substituted derivatives thereof, more preferably, the halogen and alkyl-substituted derivatives thereof.

With respect to formula IIIa, each R¹ may be independently selected from the group consisting of hydrogen, monovalent alkyl, and monovalent aryl radicals, preferably, hydrogen, monovalent $C_{1-6}$ alkyl, and phenyl radicals. Most preferably, each R¹ is selected from hydrogen, methyl, and ethyl radicals; and n is 0, 1, or 2. When n is 0, there are no carbon atoms bridging the two phenyl rings having substituents A and B; and thus the rings are connected by a single C—C bond so as to form a biphenyl ring system. More preferably, n is 0, and the composition is represented by formula IIc:

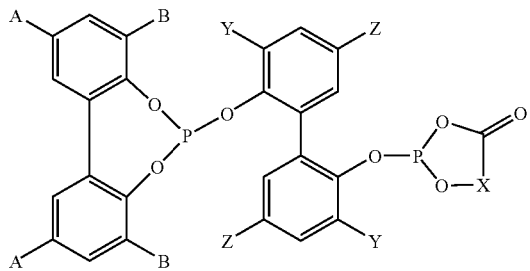

wherein A, B, Y, Z, and X are as described hereinbefore.

More preferably, the phosoxophite composition of this invention is selected from the following species:

Phosoxophite A

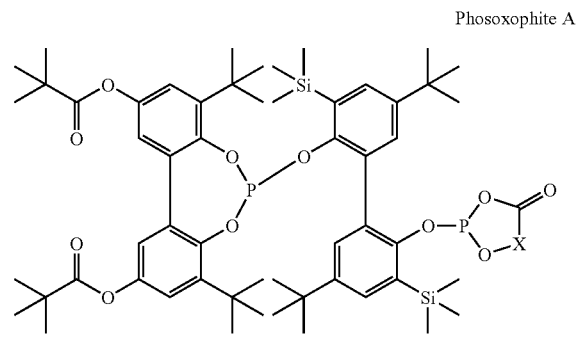

Phosoxophite B

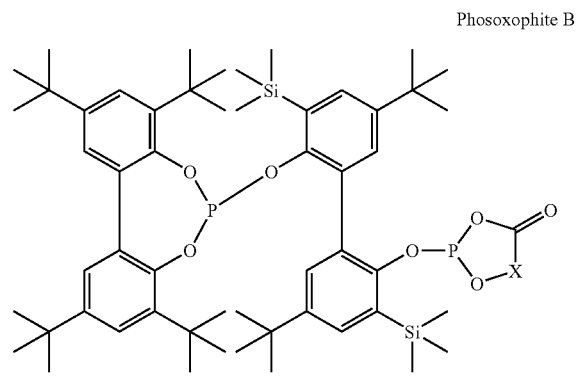

Phosoxophite C

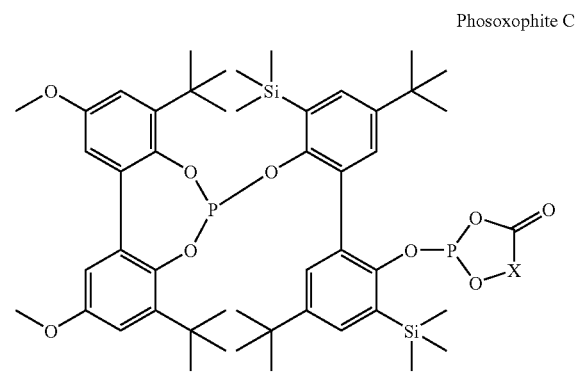

Phosoxophite D

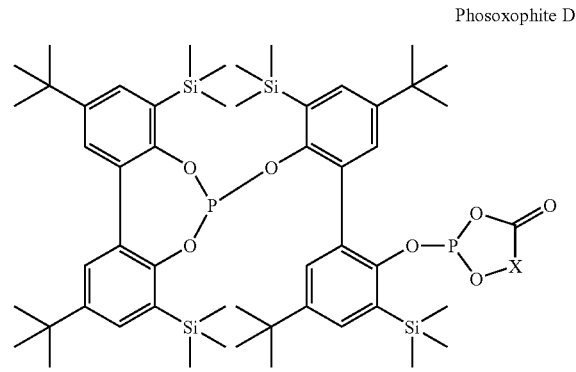

Phosoxophite E

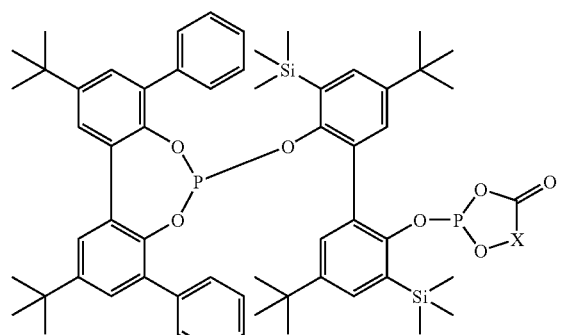

Phosoxophite I

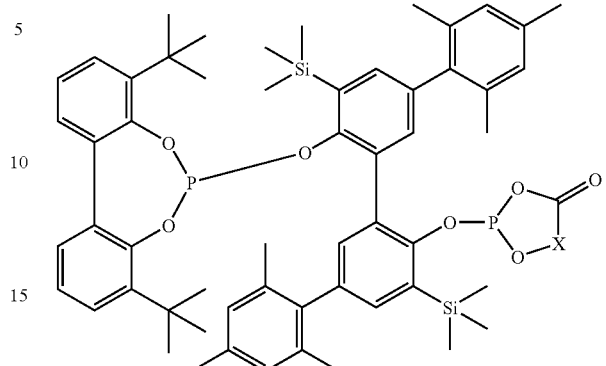

Phosoxophite F

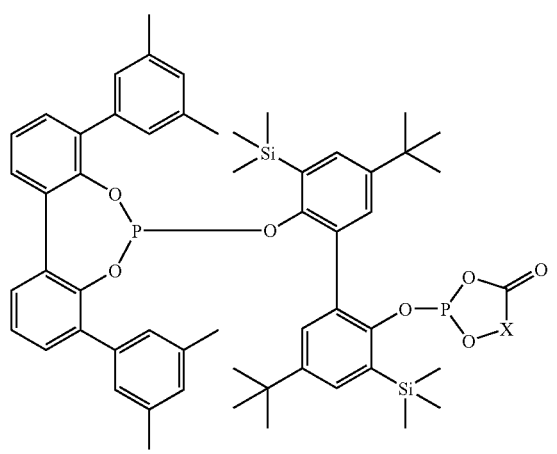

Phosoxophite J

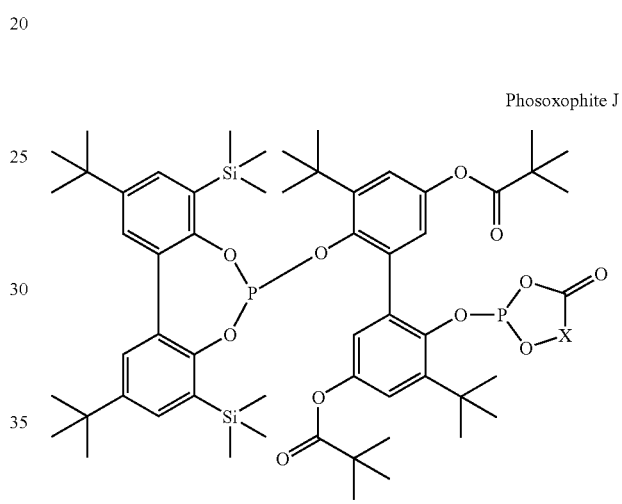

Phosoxophite G

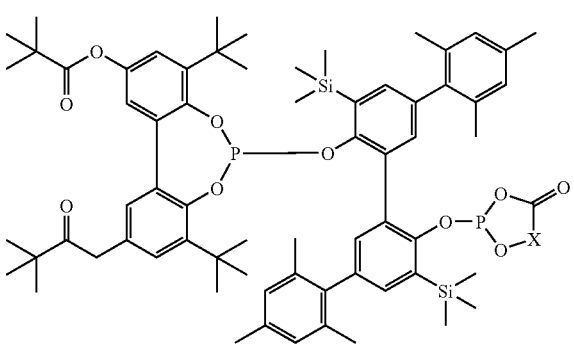

Phosoxophite K

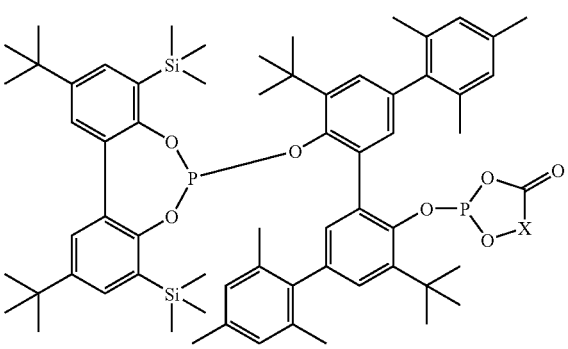

Phosoxophite H

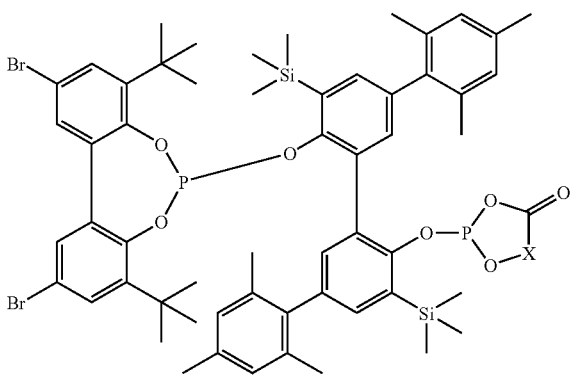

wherein, in the species formulas A through K hereinabove, X is any alkyl or aryl diradical as defined previously herein; more preferably, 1,2-phenylene, 3,5-dibromo-1,2-phenylene, 3-5-di(isopropyl)-1,2-phenylene, 1,1-diethylmethylene, 1,1-cyclohexylidene, and 1,1-cycloheptylidene.

Most preferably, the phosoxophite composition of this invention is selected from the following species:

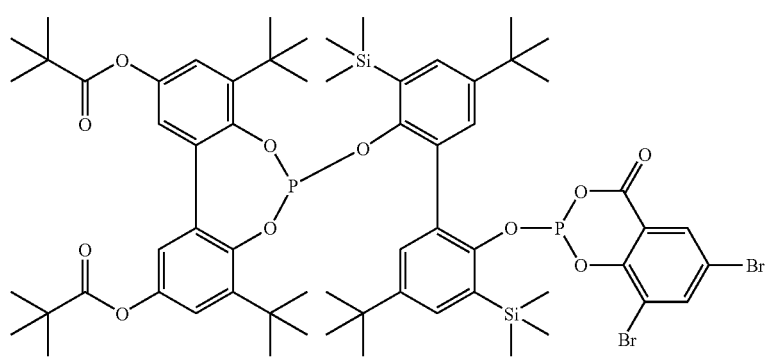
Phosoxophite M
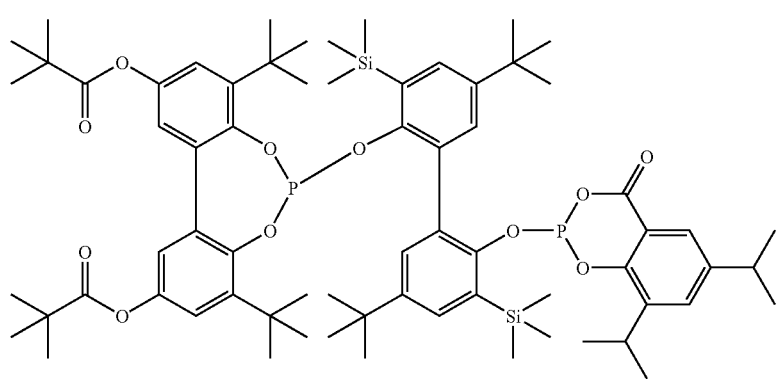
Phosoxophite N
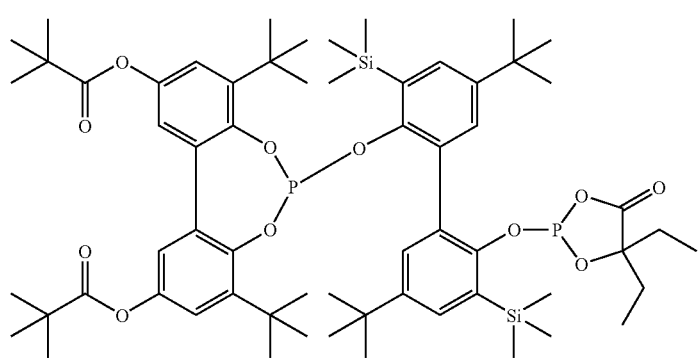
Phosoxophite O
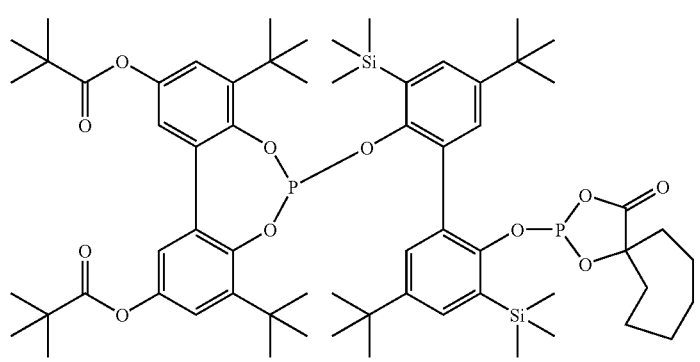
Phosoxophite P -continued
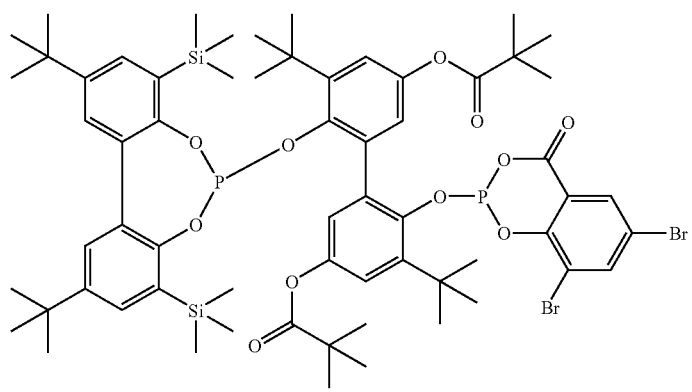
Phosoxophite Q
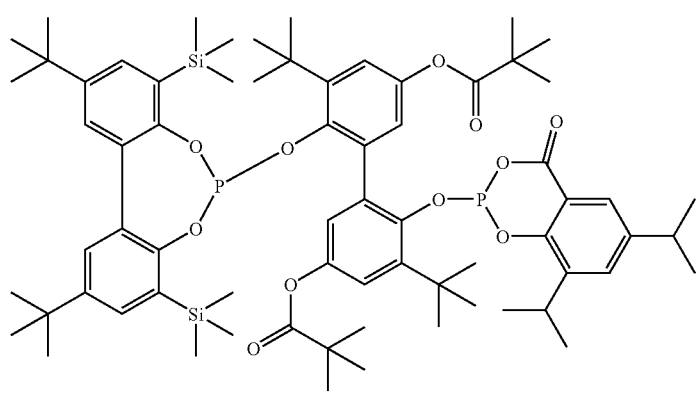
Phosoxophite R
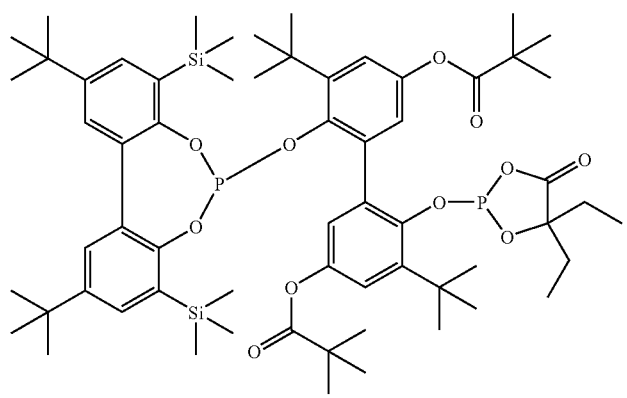
Phosoxophite S
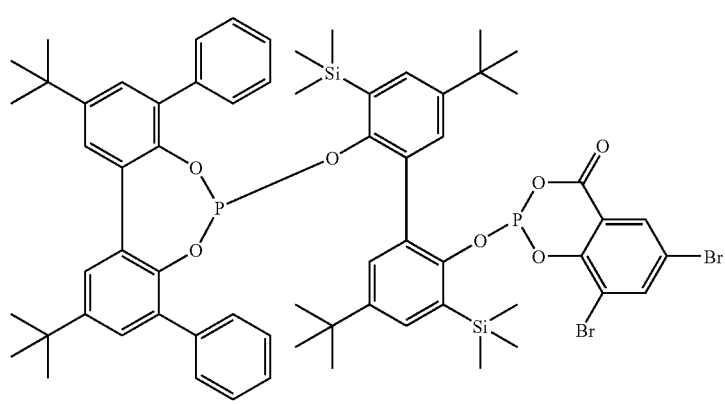
Phosoxophite T

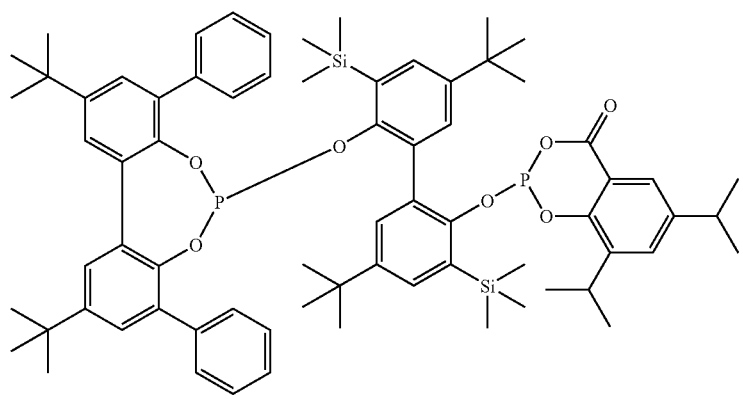
Phosoxophite U
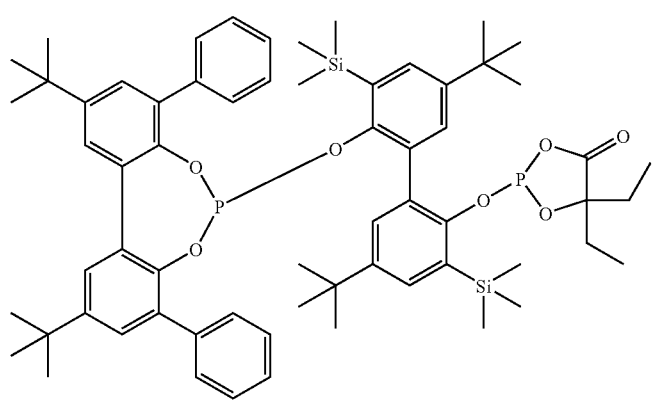
Phosoxophite V
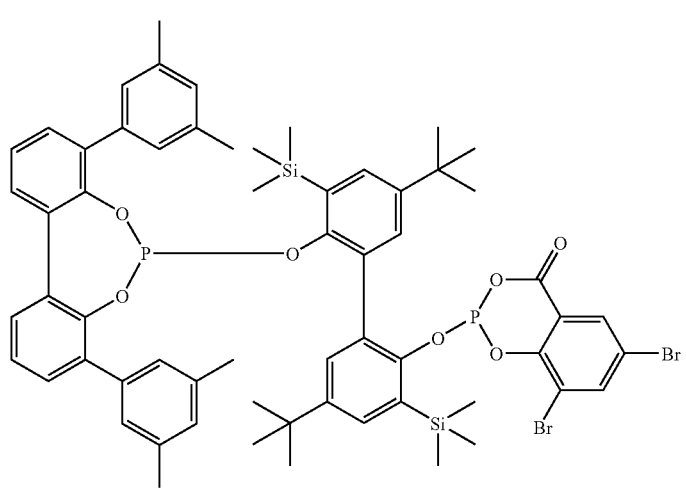
Phosoxophite W

-continued
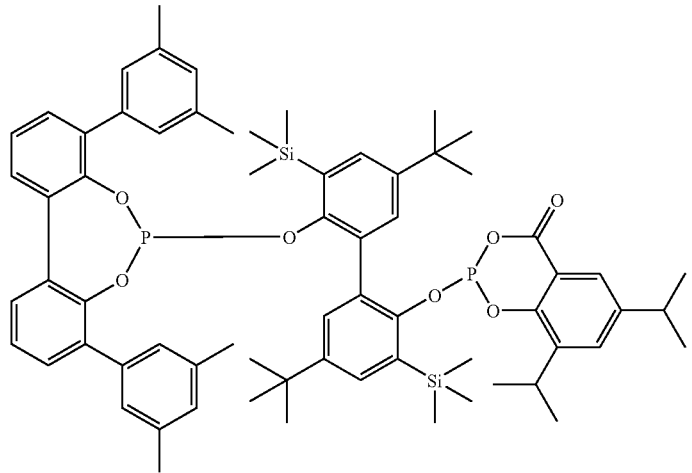
Phosoxophite X
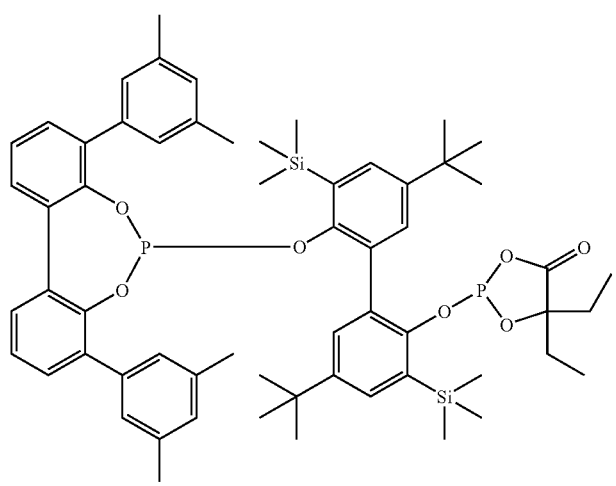
Phosoxophite Y
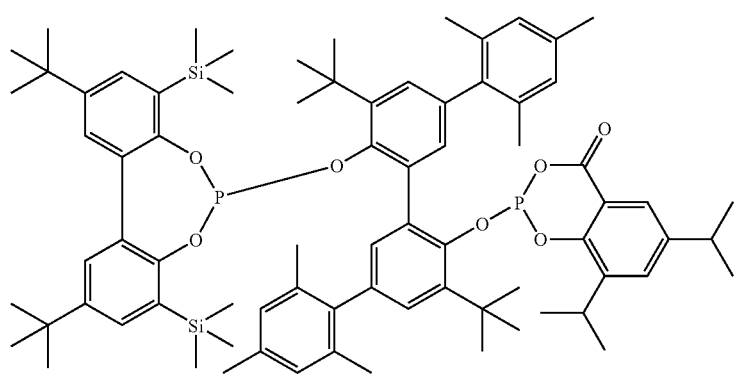
Phosoxophite Z -continued
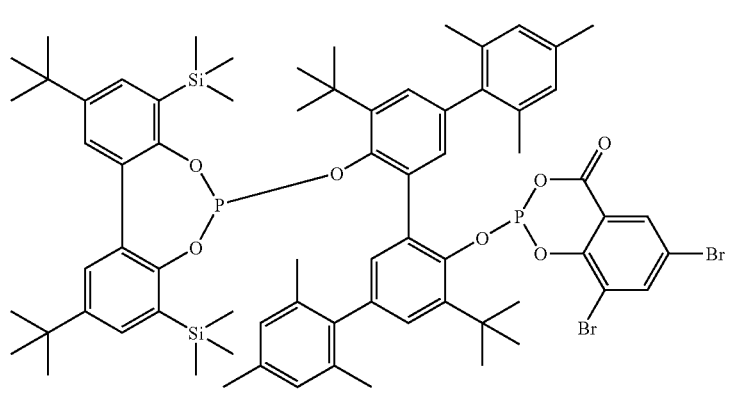
Phosoxophite AA
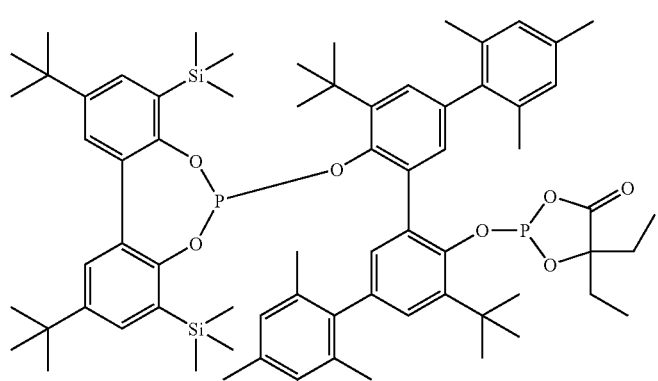
Phosoxophite BB
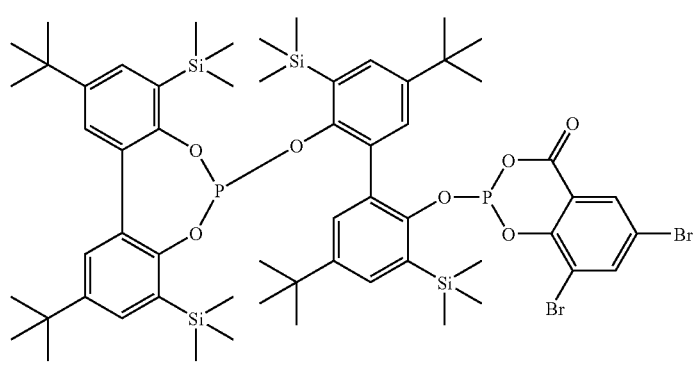
Phosoxophite CC
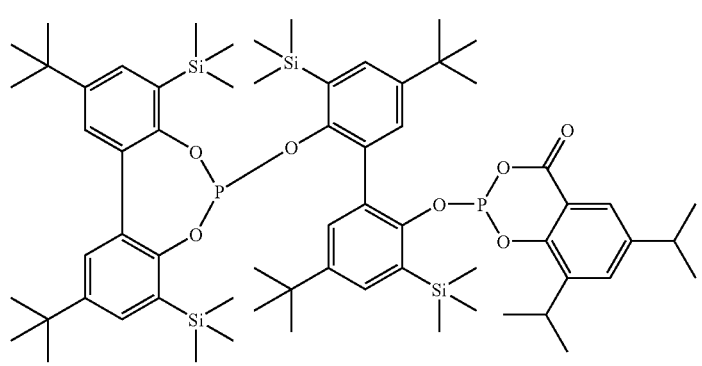
Phosoxophite DD Phosoxophite EE
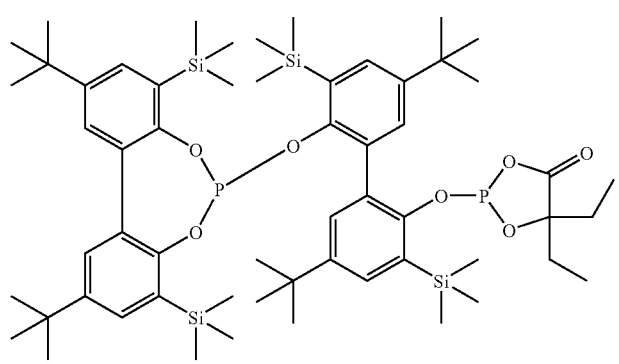
Phosoxophite FF
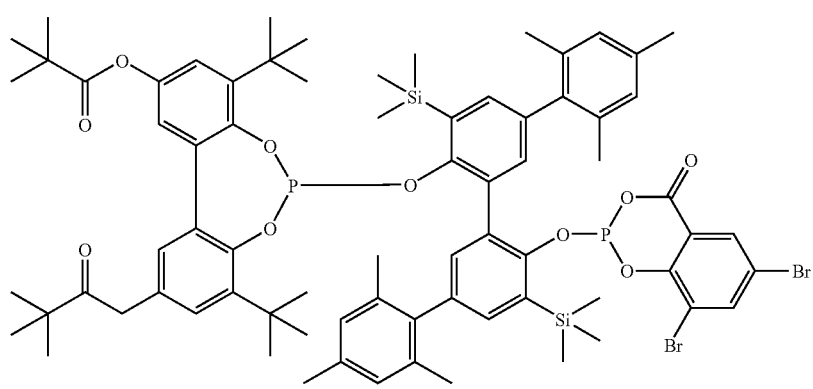
Phosoxophite GG
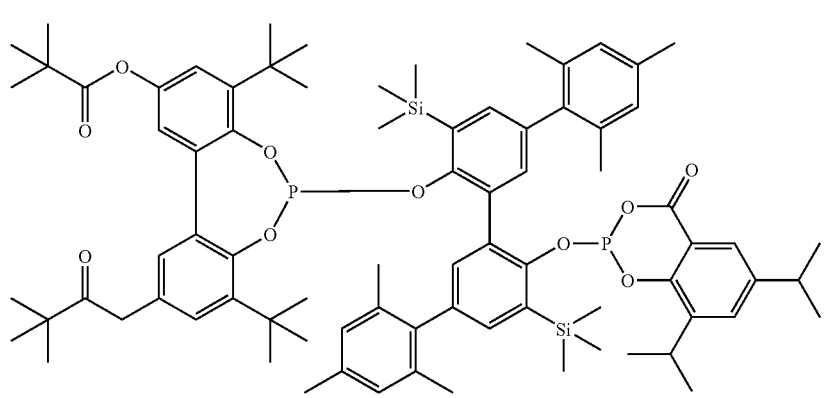
Phosoxophite HH
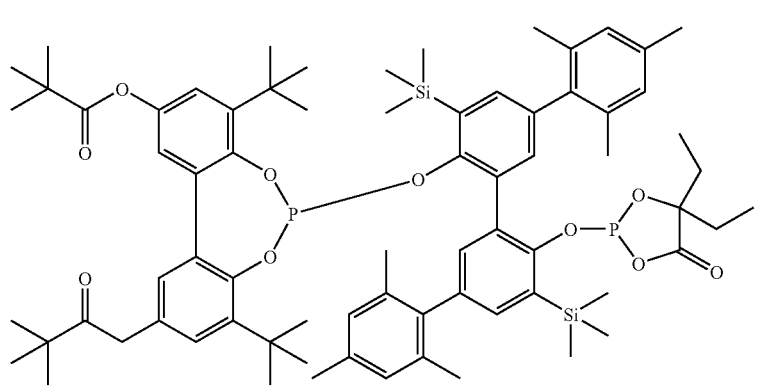

In a second aspect of this invention, the novel phosoxophite composition IIa of this invention can be readily synthesized by a novel process comprising contacting a dichloro-bisphosphite composition represented by formula IV:

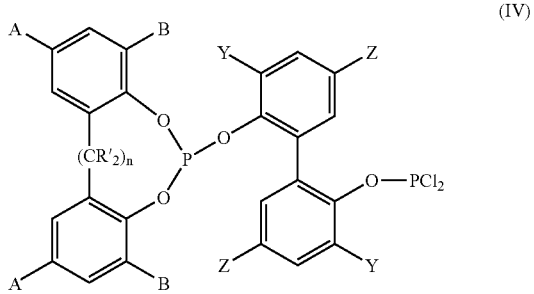

with an hydroxy acid represented by formula V:

wherein each A, B, $R^1$, n, Y, Z, and X is as defined hereinabove in connection with formula IIa. In general, the contacting of composition IV with composition V is carried out under reaction conditions sufficient to prepare the phosoxophite composition of Formula IIa. The preparation of the dichloro-bisphosphite starting material of formula IV is well known in the art, as described in EP-A1-569,328, EP-A1-353,770, EP-A1-213,639, and as disclosed by Stephen D. Pastor et al., in Inorganic Chemistry (1996), 35(4), 949–958, the aforementioned references being incorporated herein by reference. Hydroxy acids are well known and readily available.

Any quantities of dichloro-bisphosphite compound of formula IV and hydroxy acid of formula V can be employed in the synthesis reaction, provided that the novel phosoxophite composition of formula IIa is produced. Typically, the molar ratio of dichloro-bisphosphite compound of formula IV to hydroxy acid of formula V is greater than about 0.7/1. Typically, the molar ratio of dichloro-bisphosphite compound of formula IV to hydroxy acid of formula V is less than about 1.3/1. Preferably, the molar ratio of dichloro-bisphosphite compound of formula IV to hydroxy acid of formula V is about 1.0/1.0 (within ±15 percent). The condensation reaction is typically conducted in the presence of a solvent, any one of which may be employed, so long as the desired phosoxophite product of formula IIa is obtained. Preferably, the solvent is selected to solubilize the bisphosphite and hydroxyacid reactants, the hydroxy acid in particular. The usual precautions are taken to select a solvent that is non-reactive with the reactants and stable under the synthesis conditions. Ethers, more preferably, tetrahydrofuran, are the preferred solvents. The amount of solvent to be used may be readily determined by one skilled in the art. Generally, sufficient solvent is employed such that the concentrations of the dichloro-bisphosphite compound of formula IV and the hydroxy acid of formula V are each no greater than about 20 weight percent, and preferably, no greater than about 10 weight percent in the resulting solution or reaction mixture. Typically, the concentrations of the dichloro-bisphosphite compound of formula IV and the hydroxy acid of formula V are each greater than about 0.01 weight percent, and preferably, each greater than about 0.1 weight percent, in the reaction mixture.

A base is also required for the synthesis of the phosoxophite composition of formula IIa. The base may be any base that is capable of binding hydrogen chloride. Non-limiting examples of suitable bases include amines, such as alkyl amines, preferably, $C_{1-20}$ trialkyl amines, as well as basic N-heterocycles. Non-limiting examples of suitable bases include triethylamine, tripropylamine, tributylamine, and pyridine. Any quantity of base can be used, provided that the phosoxophite ligand of formula IIa is obtained in the synthesis reaction. Since two equivalents of hydrogen chloride are produced per equivalent of dichloro-bisphosphite reacted, the base is typically employed in a two-fold or greater molar excess relative to the moles of dichloro-bisphosphite compound used. Preferably, the molar ratio of base to dichloro-bisphosphite compound IV is greater than about 2.2/1, but less than about 2.7/1.

Any suitable reaction conditions can be employed for the synthesis, provided that the desired phosoxophite composition of formula IIa is produced. For example, batch reactors and continuous stirred tank reactors (CSTR) can be suitably employed. The reaction temperature is typically greater than about −35° C. and less than about 60° C. Usually, the synthesis mixture is initially prepared at about −30° C., and then the reaction temperature is allowed to rise to ambient temperature, at which temperature the synthesis may be essentially complete. If not complete, then slight heating up to about 60° C. may be employed. The synthesis is conveniently conducted at ambient pressure; but a higher or lower pressure may be used, as desired. Usually, the synthesis is conducted under an inert gaseous atmosphere, such as, nitrogen, argon, helium, or the like. The residence time of the reactants in the reactor is typically greater than about 15 minutes, preferably, greater than about 30 minutes. The residence time of the reactants in the reactor is typically less than about 10 hours, preferably, less than about 5 hours, more preferably, less than about 3 hours, and most preferably, less than about 2 hours. At the completion of the synthesis, the phosoxophite composition of formula IIa is separated or isolated from the synthesis mixture by methods known to those skilled in the art. Typically, an amine salt, resulting from the reaction of the base with the co-product hydrogen chloride, is filtered off; and the resulting product fluid is treated by standard methods including, for example, evaporation, distillation, crystallization, extraction, or tituration to yield an essentially pure phosoxophite product of formula IIa. Typically, the in situ (non-isolated) yield of phosoxophite product is greater than about 85 mole percent, preferably, greater than about 95 mole percent. The isolated yield of phosoxophite product is typically greater than about 70 mole percent, preferably, greater than about 80 mole percent, and more preferably, greater than about 90 mole percent.

In a related aspect, this invention also provides for a novel synthetic process of preparing a 2,2'-phosphoromonochloridite having the formula VI:

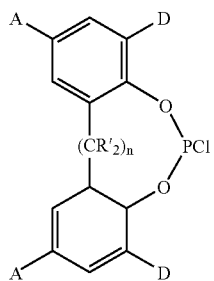

(VI)

wherein each D is independently selected from the group consisting of hydrogen, halogen, $R^4$, —C(O)$R^4$, —C(O)O$R^4$, —C(O)N$R^4{}_2$, —C(O)CF$_3$, and B, wherein each $R^4$ in any of the aforementioned formulas is a primary monovalent $C_{1-20}$ alkyl radical, and wherein each A, B, $R^1$, and n are substituents identical to those defined hereinbefore in connection with formula IIa. The phosphoromonochloridite of composition VI finds utility as a starting material in the preparation of the dichloro-bisphosphite composition of formula IV, which itself is used in the synthesis of the novel phosoxophite composition of formula IIa. Syntheses of the phosphoromonochloridite of formula VI, particularly species thereof having large and bulky substituents, may be found in the art. Usually, however, the prior art methods are unsuitable for synthesizing species having small and less bulky substituents, such as, hydrogen, halogen, and lower alkyl straight-chain moieties, for example, methyl and ethyl. Accordingly, a novel synthesis is provided herein for the phosphoromonochloridite composition of formula VI that is applicable essentially to all species, but particularly to species that have smaller and less bulky substituents, such as, hydrogen, halogen, and $C_{1-10}$ primary alkyl groups. The preferred process comprises contacting the corresponding 2,2'-biphenol VII:

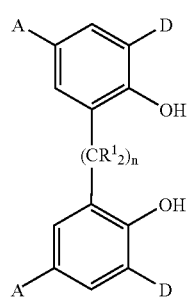

(VII)

wherein A, D, $R^1$, and n are as defined hereinbefore, with stoichiometric or excess amounts of phosphorus trichloride (PCl$_3$) in the presence of N,N-dimethylaniline under reaction conditions sufficient to prepare the phosphoromonochloridite composition of formula VI. Typically, about stoichiometric quantities of the biphenol VII, PCl$_3$, and base (1:1:2) are employed; but quantities of PCl$_3$ and the base above stoichiometry may also be employed. Any solvent that solubilizes the reagents without interfering in the reaction itself may be used, including for example, ethers, alkanes, and aromatic hydrocarbons. Preferably, the solvent is selected from tetrahydrofuran, diethyl ether, toluene, and mixtures thereof. The concentration of the reagents in the solvent ranges in each instance from greater than about 0.01 weight percent, preferably, greater than about 0.1 weight percent to less than about 20 weight percent, and preferably, less than about 10 weight percent. The process typically is conducted at a temperature greater than about −78° C., and preferably, greater than about −40° C. The process is typically conducted at a temperature less than about 60° C., preferably, less than about 40° C. Generally, the process is carried out at ambient pressure, but higher or lower pressures may be employed, if desired. Reaction under a blanket of inert atmosphere, such as nitrogen, argon, or helium, is preferred.

The aforementioned description of synthetic processes, which relates to formula IIa, the bisphosphite IV, and the phosphoromonochloridite VI, shall be equally and analogously applicable to formula IIb, with the exception that the bridging atoms or bond connecting the two phenyl rings having substituents A and B in formula IIa shall be absent in any application related to formula IIb. Accordingly, the synthetic processes should be accommodated to this difference.

The phosoxophite composition (IIa and IIb) of this invention finds a variety of applications including, for example, as a ligand in transition metal complex catalysts and catalyst precursors that are used in carbonylation processes, preferably, hydroformylation processes. Accordingly, in a third aspect this invention provides for an entirely new class of complex catalysts and complex catalyst precursor compositions that comprise a Group VIII transition metal bonded to at least one phosoxophite ligand represented by formula IIa or IIb. Optionally, the Group VIII transition metal may also be bonded to carbon monoxide, hydrogen, or both carbon monoxide and hydrogen. The Group VIII transition metal that makes up the complex catalyst or catalyst precursor composition of this invention includes those transition metals selected from the group consisting of rhodium (Rh), cobalt (Co), iridium (Ir), ruthenium (Ru), iron (Fe), nickel (Ni), palladium (Pd), platinum (Pt), and osmium (Os), and mixtures thereof, with the preferred metals being ruthenium, rhodium, cobalt, and iridium, more preferably, rhodium and cobalt, and most preferably, rhodium. The term "complex" as used herein shall be taken to mean a coordination compound formed by the union of one or more ligands, herein one or more phosoxophite ligands of formula IIa or IIb, with a Group VIII metal. Inherently, the phosoxophite ligands are electronically rich, since each ligand possesses two phosphorus donor atoms, each of which possesses one available or unshared pair of electrons that is capable of forming a coordinate covalent bond independently or in concert (e.g., via chelation) with the Group VIII transition metal. The oxidation state of the Group VIII metal may be any available oxidation state, both electronically neutral (zero) or electronically deficient (positive valence) that allows for bonding to the phosoxopoite ligand. Moreover, the oxidation state of the Group VIII transition metal as well as the overall oxidation state of the coordination complex or complex precursor may vary during use in the carbonylation process. The number of available coordination sites on the Group VIII transition metal is well known in the art and may range typically from about 4 to about 6. Optionally, the Group VIII transition metal may be additionally bonded to carbon monoxide, hydrogen, or both carbon monoxide and hydrogen.

In a fourth and related aspect, this invention can be described as a novel transition metal complex catalyst or catalyst precursor solution comprising an organic solvent, a solubilized Group VIII transition metal-phosoxophite ligand complex, and free phosoxophite ligand, wherein the phosoxophite ligand is represented by formula IIa or IIb hereinabove. Such novel solutions may be prepared by forming a solution comprising an organic solvent, free phosoxophite ligand, and a Group VIII transition metal source material, such as the corresponding transition metal oxide, hydride, carbonyl, salt, or organotransition metal complex, as described hereinafter, and thereafter subjecting such solution to reaction conditions sufficient to bind at least a portion of the phosoxophite ligand to the Group VIII transition metal. Optionally, carbon monoxide and hydrogen may be dissolved in the solution and bonded to the Group VIII transition metal.

As in the case of prior art Group VIII metal-phosphorus complex catalysts, the Group VIII transition metal-phosoxophite complex catalyst of this invention may be formed by methods known in the art. For instance, Group VIII transition metal hydrido-carbonyl(phosoxophite) catalysts may be preformed and introduced into the reaction medium of a carbonylation process. Standard identification methods may be used to identify the complex catalyst or catalyst precursor composition, including for example, elemental analysis, mass spectroscopy, infrared spectroscopy, and $H^1$, $P^{31}$, and/or $C^{13}$ NMR spectroscopy, and the like.

Preferably, the Group VIII transition metal-phosoxophite complex catalyst of this invention is derived from a Group VIII transition metal source material that is introduced into a carbonylation reaction medium for in situ formation of the active catalyst. For example, rhodium source materials, such as, rhodium acetylacetonate, rhodium dicarbonyl acetylacetonate, $Rh_2O_3$, $Rh_4(CO)_{12}$, $[RhCl(CO)_2]_2$, $Rh_6(CO)_{16}$, $Rh(NO_3)_3$, and the like may be introduced into the carbonylation reaction medium along with the phosoxophite ligand for the in situ formation of the active catalyst. In a preferred embodiment, rhodium dicarbonyl acetylacetonate is employed as a rhodium source material and reacted in the presence of a solvent with the phosoxophite to form a catalytic rhodium-phosoxophite complex precursor composition, which is introduced into the reactor along with excess free phosoxophite ligand for the in situ formation of the active catalyst. In any event, it is sufficient for the purpose of this invention to understand that carbon monoxide, hydrogen, and phosoxophite are all ligands that are capable of being complexed with the Group VIII transition metal, e.g., rhodium, and that an active Group VIII transition metal-phosoxophite catalyst is present in the reaction medium under the conditions of the carbonylation, and preferably, hydroformylation process. The reaction conditions sufficient for formation of the complex catalyst or catalyst precursor in most cases will be similar to the carbonylation reaction conditions described hereinbelow.

In a preferred embodiment the Group VIII transition metal-phosoxophite complex catalyst composition of this invention may be defined as comprising a Group VIII transition metal complexed with carbon monoxide and at least one phosoxophite ligand, said ligand being bonded (i.e., complexed) to the metal in a chelated or non-chelated fashion. Moreover, the term "comprising" is also meant to include hydrogen complexed with the metal, particularly in the case of rhodium-catalyzed hydroformylation processes wherein hydrogen is also present in the reaction mixture. As noted hereinabove, the carbonyl and/or hydrogen ligands of an active rhodium phosoxophite complex catalyst may be present as a result of being ligands bound to a Group VIII transition metal source material, or as a result of being ligands bound to a Group VIII transition metal complex precursor composition, and/or as a result of in situ formation due to hydrogen and carbon monoxide being employed in the hydroformylation process.

In a fifth aspect, this invention provides for a carbonylation process, which comprises contacting an organic compound capable of being carbonylated with carbon monoxide in the presence of the Group VIII transition metal-phosoxophite ligand complex catalyst mentioned above, wherein the phosoxophite ligand is represented by formula IIa or IIb. Such processes may include the carbonylation of organic compounds, such as olefins, acetylenes, alcohols, and activated chlorides, with carbon monoxide, and optionally, either hydrogen, alcohol, amine, or water, as well as ring closure reactions of functionally unsaturated compounds, e.g., unsaturated amides, with carbon monoxide. Exemplary carbonylation processes include, for example, simple carbonylation (insertion of carbonyl in absence of other reactant), hydroformylation, hydroacylation (intermolecular and intramolecular), hydrocyanation, hydroamidation, hydroesterification, and hydrocarboxylation processes. The contacting in such a process is conducted under carbonylation conditions sufficient to prepare the corresponding carbonylated organic compound. In a preferred embodiment, the carbonylation process also contains free phosoxophite ligand, in addition to the phosoxophite ligand bonded to the Group VIII transition metal. Preferably, the carbonylation process involves a hydroformylation process, more preferably, the hydroformylation of an olefin with carbon monoxide in the presence of hydrogen to prepare an aldehyde. The more preferred carbonylation process to prepare aldehydes is known in industry under varying names including the "oxo" process, the "oxo" reaction, "oxonation," the "Roelen reaction," or more commonly, simply "hydroformylation." The processing techniques employed in the carbonylation process of this invention correspond to any of the known processing techniques employed in conventional carbonylation processes, or hydroformylation processes, as described in detail hereinafter.

It is to be noted that the successful practice of this carbonylation process invention does not depend and is not predicated upon the exact formula of the catalytically active metal complex species, which may be present in a mononuclear, dinuclear, or higher nuclearity form. Indeed, the exact formula of the catalytically active metal ligand complex may be difficult to determine analytically. Although not intended to be bound to any theory or mechanistic discourse, it appears that the active catalytic species in its general form comprises the Group VIII transition metal in complex combination with one or more phosoxophite ligands of formula IIa or IIb, further in combination with carbon monoxide, since carbon monoxide is also present and capable of complexing to the Group VIII transition metal. As noted previously, the ultimate composition of the active complex may also contain one or more additional ligands, such as hydrogen, or an anion satisfying the coordination sites or nuclear charge of the Group VIII transition metal, as the case may be, obtained typically from the starting transition metal material. Illustrative additional ligands include halogen ($Cl^-$, $Br^-$, $I^-$), alkyl, aryl, substituted aryl, $CF_3^-$, $C_2F_5^-$, $CN^-$, $R'_2PO^-$, $R'P(O)(OH)O^-$ (wherein each R' is alkyl or aryl), $CH_3C(O)O^-$, acetylacetonate, $SO_4^{2-}$, $PF_4^-$, $PF_6^-$, $NO_2^-$, $NO_3^-$, $CH_3O^-$, $CH_2=CHCH_2^-$, $C_6H_5CN$, $CH_3CH=$, NO, $NH_3$, pyridine, $(C_2H_5)_3N$, mono-olefins, diolefins, triolefins, tetrahydrofuran, and the like. Of course, it is to be understood that the active complex species is preferably free of any additional organic ligand or anion that might poison the catalyst and have an undue adverse effect on the catalyst performance. For instance, in conventional rhodium-catalyzed hydroformylation processes halogen atoms and sulfur atoms may typically poison the catalyst. Accordingly, it is preferred that in the rhodium-catalyzed hydroformylation reaction of this invention that the active catalyst also be free of halogen and sulfur directly bonded to the rhodium, although such requirement may not be absolutely necessary.

Any amount of complex catalyst can be employed in the carbonylation reaction medium, provided that the amount is sufficient to catalyze the desired carbonylation process. In general, the concentration of complex catalyst provides for a concentration of Group VIII transition metal of greater than about 10 parts per million (ppm), preferably, greater than about 25 ppm, by weight calculated as free metal. Generally, the concentration of complex catalyst provides for a concentration of Group VIII transition metal of less than about 1,000 ppm preferably, less than about 800 ppm, and more preferably, less than about 600 ppm, by weight calculated as free metal.

The olefinic reactants to be used in the preferred carbonylation process of this invention can be any terminally or internally olefinically-unsaturated aliphatic hydrocarbon, including straight chain, branched chain, and cyclic formulas. Such olefins contain preferably from 2 to 20 carbon atoms and one or more unsaturated groups. Moreover, such olefins may contain substituents that essentially do not adversely interfere with the hydroformylation process, including, for example, carbonyl, carbonyloxy, hydroxy, oxycarbonyl, halo, alkyoxy, aryl, haloalkyl, and the like. Non-limiting examples of suitable olefinic unsaturated reactants include, for example, alpha olefins, internal olefins, alkyl alkenoates, alkenyl alkanoates, alkenyl alkyl ethers, alkenols, and the like; more specifically, ethylene, propylene, 1-butene, 1-pentene, 1-hexene, 1-octene, 1-decene, 1-dodecene, 1-octadecene, 2-butene, 2-methyl propene (isobutylene), isoamylene, 2-pentene, 2'-hexene, 3-hexene, 2-heptene, cyclohexene, propylene dimers, propylene trimers, propylene tetramers, 2-ethylhexene, styrene, 3-phenyl-1-propene, butadiene, 1,3-cyclohexadiene, 1,4-cyclohexadiene, 1,7-octadiene, 3-cyclohexyl-1-butene, allyl alcohol, hex-1-en-4-ol, oct-1-ene-4-ol, vinyl acetate, allyl acetate, 3-butenyl acetate, vinyl propionate, 1-vinyl-3-cyclohexene, allyl propionate, allyl butyrate, methyl methacrylate, 3-butenyl acetate, vinyl ether, vinyl methyl ether, allyl ethyl ether, n-propyl-7-octenoate, methyl 1-decenoate, 3-butenenitrile, 5-hexenamide, methyl oleate, castor oil, soybean oil and the like. Mixtures of olefinic starting materials can be employed, if desired. Preferably, the carbonylation process is especially useful for the production of aldehydes by the hydroformylation of alpha olefins containing from 2 to about 60 carbon atoms and internal olefins containing from 4 to about 60 carbon atoms, as well as mixtures of such alpha and internal olefins.

The carbonylation process, and preferably hydroformylation process, of this invention is also preferably conducted in the presence of an organic solvent for the Group VIII transition metal complex catalyst. Any suitable solvent that does not unduly interfere with the carbonylation process can be used, including those types of solvents commonly used in prior art carbonylation processes. By way of illustration, suitable solvents for rhodium catalyzed hydroformylation processes include those disclosed, for example, in U.S. Pat. No. 3,527,809; U.S. Pat. No. 4,148,830; and U.S. Pat. No. 5,929,289, the aforementioned citations being incorporated herein by reference. Non-limiting examples of suitable solvents include saturated hydrocarbons, aromatic hydrocarbons, ethers, aldehydes, ketones, nitrites, and aldehyde condensation products. More specific solvents, for example, include the following solvents: tetraglyme, pentanes, cyclohexane, benzene, xylene, toluene, diethyl ether, tetrahydrofuran, butyraldehyde, and benzonitrile. Mixtures of two or more solvents may also be employed. In rhodium catalyzed hydroformylation processes, it may be preferred to employ as the primary solvent aldehyde compounds corresponding to the aldehyde products desired to be produced and/or higher boiling aldehyde liquid condensation by-products, for example, as might be produced in situ during the hydroformylation process, as described for example in U.S. Pat. No. 4,148,380 and U.S. Pat. No. 4,247,486, incorporated herein by reference. Indeed, while one may employ, if desired, any suitable solvent at the start-up of a continuous process, the primary solvent will normally eventually comprise both aldehyde products and higher boiling aldehyde liquid condensation by-products, due to the nature of such continuous processes. The amount of solvent is not especially critical and need only be sufficient to provide the reaction medium with the desired amount of Group VIII transition metal concentration. Typically, the amount of solvent ranges from about 5 percent to about 95 percent by weight, based on the total weight of the reaction medium.

The carbonylation process of this invention may preferably be conducted in the presence of free phosoxophite ligand, that is, ligand that is not complexed with the Group VIII transition metal. The use of free phosoxdphite ligand may not be absolutely necessary, however. The free phosoxophite ligand may correspond to any of the phosoxophite ligand species illustrated hereinabove. While it is preferred to employ a free phosbxophite ligand that is the same as the phosoxophite ligand complexed to the transition metal in the Group VIII-phosoxophite complex catalyst, it is not absolutely required for the free and complexed phosoxophite ligands to be the same. The free and complexed phosoxophite ligands may be different, if desired. While the carbonylation process of this invention may be carried out in any excess amount of free phosoxophite ligand, typically at least one mole of free phosoxophite ligand per mole of Group VIII transition metal is present in the reaction medium. For most purposes, preferably, the amount of phosoxophite ligand per mole of Group VIII transition metal is greater than about 1.2/1, more preferably, greater than about 1.5/1 is employed. Preferably, the amount of phosoxophite ligand per mole of Group VIII transition metal is less than about 100/1, more preferably, less than about 50/1. The aforementioned ratios correspond to the sum of both the free and complexed phosoxophite ligand. Make-up phosoxophite ligand can be added during the carbonylation process at any time and in any suitable manner, so as to maintain a predetermined concentration of free ligand in the reaction medium.

The reaction conditions for effecting carbonylation can be chosen from any of those conditions conventionally used and known for such processes. Generally, the carbonylation process temperature is greater than about 30° C., preferably, greater than about 40° C. Generally, the carbonylation process temperature is less than about 200° C., preferably, less than about 120° C. Pressures greater than about 1 psia (7 kPa) to less than about 10,000 psia (68,948 kPa) are usually employed. The carbonylation process may be conducted as a single pass, continuous process. Alternatively, the carbonylation process may include recycle of any unreacted olefin reagent for multiple pass, continuous processing.

As noted herein, the preferred carbonaylation process involves contacting an olefin with carbon monoxide and hydrogen under reaction conditions sufficient to prepare an aldehyde. The total gas pressure of hydrogen, carbon monoxide, and olefinic unsaturated reactant in the hydroformylation process may range from greater than about 1 psia (7 kPa) to less than about 10,000psia (68,948 kPa). Preferably, the total pressure of hydrogen, carbon monoxide, and olefinic unsaturated reactant is less than about 2000 psia (13,790 kPa), and more preferably, less than about 1500 psia (10,343 kPa). More specifically, the carbon monoxide partial pressure of the hydroformylation process of this invention is typically greater than about 1 psia (7 kPa), preferably, greater than about 3 psia (21 kPa). The carbon monoxide partial pressure of the hydroformylation process of this invention is typically less than about 1000 psia (6,895 kPa), preferably, less than about 750 psia (5171 kPa). The hydrogen partial pressure is typically greater than about 5 psia (35 psia), preferably, greater than about 10 psia (69 kPa). The hydrogen partial pressure is typically less than about 1000 psia (6,896 kPa), preferably, less than about 750 psia (5171 kPa). In general, the $H_2/CO$ molar ratio of gaseous hydrogen to carbon monoxide may be greater than about 1/10, and preferably, equal to or greater than about 1/1. The $H_2/CO$ molar ratio may be less than about 100/1, and preferably, equal to or less than about 10/1.

Further to the hydroformylation process of this invention, the reaction temperature will depend upon the particular olefinic reagent and metal catalyst employed, as well as the efficiency desired. Generally, hydroformylations at reaction temperatures of greater than about 30° C., and preferably, greater than about 40° C., are suitable. Generally, hydroformylations at reaction temperatures of less than about 150° C., and preferably, less than about 120° C., are suitable. Alpha-olefins are more preferably hydroformylated at a temperature of greater than about 40° C. and less than about 80° C.; whereas less reactive olefins, such as isobutylene and internal olefins, are more preferably hydroformylated at a temperature greater than about 50° C. and less than about 120° C.

The carbonylation process, and preferred hydroformylation process, of this invention can be carried out in the liquid or gas phase, or preferably, in mixed liquid and gas phases, which can more preferably involve a continuous liquid phase and a gas phase recycle system or combination of recycle systems. In a preferred embodiment, the process involves a continuous homogeneous catalysis process wherein carbonylation is carried out in the presence of free phosoxophite ligand and any conventional solvent, as described hereinabove.

In the preferred hydroformylation process of this invention, the olefin conversion is generally greater than about 70 mole percent. For the purposes of this invention, "olefin conversion" shall be defined as the mole percentage of olefin feed converted to all products. Olefin conversion will vary depending upon the specific olefin reactant, the specific form of the catalyst, and the specific process conditions employed. Preferably, the olefin conversion is greater than about 80 mole percent, more preferably, greater than about 90 mole percent, and most preferably, greater than about 95 mole percent.

Likewise, in the preferred hydroformylation process of this invention, the yield of aldehyde product, e.g., 6-hydroxyhexanal, achieved is generally greater than about 70 mole percent. For the purposes of this invention, "yield" will be defined as the mole percentage of aldehyde product produced, based on the total moles of olefin fed to the process. Again, the yield of aldehyde produced will vary based on the specific olefin reactant, the specific form of the catalyst, and the specific process conditions employed. Preferably, the yield of aldehyde is greater than about 75 mole percent, more preferably, greater than about 80 mole percent, and most preferably, greater than about 85 mole percent.

An additional advantage of the process of this invention resides in the high molar ratio of normal (linear) to iso (branched) (N:I) aldehyde products achieved, when normal aldehydes are the desired products. Typically, the N:I molar ratio is greater than about 10:1, preferably, greater than about 20:1, more preferably, greater than about 30:1, and most preferably, greater than about 50:1. In some instances, an N:I molar ratio of greater than 100:1 is observed. The process of this invention also exhibits acceptable rates of reaction and desirably low selectivities to isomerization products and hydrogenated products.

Finally, the aldehyde products of the hydroformylation process have a wide range of utility that is well known and documented in the prior art, for example, they are especially useful as starting materials for the production of alcohols and acids.

The following examples are illustrative of the present invention and are not to be regarded as limiting thereof. Variations in operational parameters, such as reactants, process conditions, forms of the transition metal ligand complex catalyst, and phosoxophite ligand species, which all fall within the scope of the claims, will be apparent to those skilled in the art, based on the description and examples contained herein. All of the parts, percentages, and proportions referred to herein are given by weight, unless otherwise indicated.

EXAMPLE 1

Preparation of Phosphoromonochloridite 3,3'-Di-t-butyl-5,5'-di-t-pivaloyloxy-2,2'-biphenylphosphoromonochloridite (PIV-PCl) of the following formula

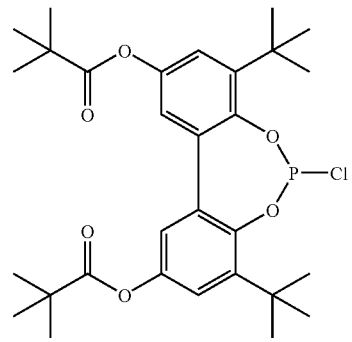

was prepared as follows. To a 250 ml round bottom flask were added 3,3'-di-t-butyl-5,5'-di-t-pivaloyloxy-2,2'-biphenol (PIV-diol) (7.63 g, 15.3 mmol), diethyl ether (80 ml), tetrahydrofuran (40 ml), and N,N-dimethylaniline (DMA, 3.90 g, 32.2 mmol). Phosphorus trichloride (2.20 g, 16.0 mmol) was placed in a separate flask and diluted with diethyl ether (10 ml). After cooling both solutions to −30° C., the ether solution containing the phosphorus trichloride was quickly added to the THF-ether solution containing the PIV-diol and DMA. After stirring for 1 h, during which time the solution was warmed to ambient temperature, a $^{31}P$ NMR sample was taken. The NMR data, which was acquired immediately, showed the reaction to be complete. A solid product, including the hydrochloride salt of N,N-dimethylaniline, was filtered and washed with ether. The filtrate was evaporated almost to dryness to yield a second solid product. Toluene (15 ml) was added to the second solid product and then evaporated to remove $PCl_3$ yielding a crude white solid product. The crude product was triturated in acetonitrile for 30 min; purified product was collected by filtration. Two additional crops of crystals were obtained from the filtrate. Combined yield of purified PIV-PCl product (6.26 g, 73%; $^{31}P$ NMR$\{^1H\}$ (122 MHz, $CDCl_3$, δ): 172 ppm).

EXAMPLE 2

Preparation of Phosoxophite Composition of Formula M

A dichloro-bisphosphite composition (PIV-TMS-PCl$_2$) having the formula shown below was prepared as follows:

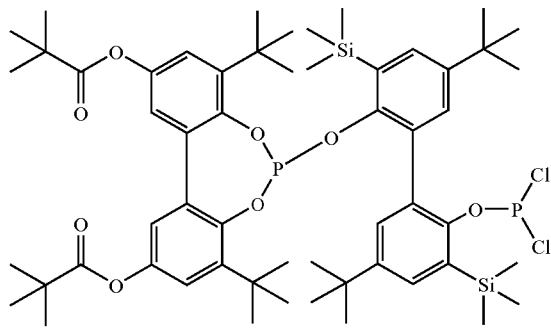

To a cold (−30° C.) solution containing tetrahydrofuran (10 ml), triethylamine (0.537 g, 5.062 mmol), and phosphoromonochloridite PIV-PCl from Example 1 (3.00 g, 5.38 mmol) was added quickly a cold (−30° C.) solution-containing tetrahydrofuran (10 ml) and 3,3'-bis(trimethylsilyl)-5,5'-di-t-butyl-2,2'-biphenol (TMS-diol) (2.358 g, 5.325 mmol). After stirring the resulting reaction mixture for 30 min at ambient temperature, a triethylamine hydrochloride salt was removed by filtration. After cooling the filtrate to −30° C., PCl$_3$ (1.08 g, 7.86 mmol) was added followed by triethylamine (0.75 g, 7.86 mmol). The reaction mixture was stirred for one hour at room temperature. Then, a second batch of triethylamine hydrochloride salt was removed by filtration. The filtrate was evaporated to dryness and the solid residue triturated in acetonitrile to yield purified PIV-TMS-PCl$_2$. Yield from the combined two steps: 4.79 g, 88%. $^{31}$P {$^1$H} NMR (121.66 MHz, THF, δ) of PIV-TMS-PCl$_2$: Major diastereomer (90%): 139.64 and 203.57 ppm (d, $J_{P-P}$=3.8 Hz, 0.9 P each); Minor diastereomer (10%): 142.08 and 202.88 ppm (s, 0.1 P each).

A novel phosoxophite composition having generic formula A and specific formula M, shown hereinabove, was prepared as follows. A first solution was prepared by dissolving 3,5-dibromosalicylic acid (1.40 g, 4.59 mmol) and triethylamine (1.20 g, 11.9 mmol) in tetrahydrofuran (10 ml). A second solution was prepared by dissolving the PIV-TMS-PCl$_2$ (4.91 g, 4.59 mmol), prepared hereinabove, in tetrahydrofuran (50 ml). Both solutions were cooled to −30° C. and the first solution was added to the second solution. The resulting mixture was stirred, allowed to warm to room temperature, and then filtered to remove triethylamine hydrochloride salt. The filtrate was evaporated, and the resulting solid residue triturated in acetonitrile. The acetonitrile mixture was filtered and dried to yield a phosoxophite composition of formula M (5.34 g, 90 percent isolated yield). Four diastereomers were observed in $^{31}$P {$^1$H} NMR spectrum in the ratio close to 61:23:13:3. $^{31}$P {$^1$H} NMR (121.66 MHz, THF, δ): diastereomer 1 (61%): 121.39 and 140.50 ppm (d, $J_{P-P}$=4.1 Hz); diastereomer 2 (23%): 116.53 and 140.74 ppm (d, $J_{P-P}$=10.1 Hz); diastereomer 3 (13%): 120.89 and 143.09 ppm (s); diastereomer 4 (3%): 116.06 and 140.50 ppm(s).

EXAMPLE 3

Organophosoxosphite Ligands and Hydroformylation Process

Phosoxophite ligands N, O, Q, R, FF, and GG, shown in the most preferred example list hereinabove, were synthesized in a manner analogous to the preparation given for phosoxophite composition M in Example 2. The following specific reactants were used.

Phosoxophite N was prepared by reacting PIV-TMS-PCl$_2$, prepared in Example 2, with 3,5-diisopropylsalicylic acid. Purified yield: 80%. Four diastereomers were observed in $^{31}$P {$^1$H} NMR spectrum in the ratio close to 56:26:15:3. $^{31}$P {$^1$H} NMR (121.66 MHz, CDCl$_3$, δ): diastereomer 1 (56%): 120.84 and 140.26 ppm(s); diastereomer 2 (26%): 117.48 and 141.05 ppm (d, $J_{P-P}$=9.5 Hz); diastereomer 3 (15%): 121.30 and 143.11 ppm(s); diastereomer 4 (3%): 117.35 and 140.82 ppm(s).

Phosoxophite O was prepared by reacting PIV-TMS-PCl$_2$, prepared in Example 2, with 2-ethyl-2-hydroxybutyric acid. Purified yield: 95%. Four diastereomers were observed in $^{31}$P {$^1$H} NMR spectrum in the ratio close to 45:33:12:10. $^{31}$P {$^1$H} NMR (121.66 MHz, THF, δ): diastereomer 1 (45%): 135.65 and 140.74 ppm (d, $J_{P-P}$=8.1 Hz); diastereomer 2 (33%): 134.98 and 140.54 ppm (d, $J_{P-P}$=3.6 Hz); diastereomer 3 (12%): 136.79 and 142.43 ppm(s); diastereomer 4 (100%): 136.24 and 141.85 ppm(s).

Phosoxophite Q was prepared by reacting 3,3'-di(trimethylsilyl)-5,5'-di-t-butyl-2,2'-biphenol with phosphorus trichloride to yield the corresponding phosphordmonchloridite TMS-PCl, which was reacted with 3,3'-di-t-butyl-5,5'-di-t-pivaloyloxy-2,2'-biphenol (PIV-diol) and phosphorus trichloride to yield the corresponding dichloro-bisphosphite product TMS-PIV-PCl$_2$, which was reacted with 3,5-dibromosalicylic acid to yield phosoxophite Q. Purified yield: 90%. Three diastereomers were observed in $^{31}$P {$^1$H} NMR spectrum in the ratio close to 77:20:3. $^{31}$P {$^1$H} NMR (121.66 MHz, CDCl$_3$, δ): diastereomer 1 (77%): 119.88 and 143.38 ppm (d, $J_{P-P}$=3.5 Hz); diastereomer 2 (20%): 116.52 and 142.16 ppm (d, $J_{P-P}$=25.7 Hz); diastereomer 3 (3%): 117.22 and 141.55 ppm(s). Phosoxophite R was prepared by reacting the TMS-PIV-PCl$_2$, prepared hereinabove, with 3,5-diisopropylsalicylic acid. Purified yield: 85%. Two diastereomers were observed in $^{31}$P {$^1$H} NMR spectrum in the ratio close to 82:18. $^{31}$P {$^1$H} NMR (121.66 MHz, CDCl$_3$, δ): diastereomer 1 (82%): 120.35 and 143.30 ppm (d, $J_{P-P}$=5.4 Hz); diastereomer 2 (18%): 117.46 and 143.15 ppm (d, $J_{P-P}$=25.3 Hz);

Phosoxophite FF was prepared by reacting the monochloridite PIV-PCl, prepared in example 1, with 3,3'-di(trimethylsilyl)-5,5'-di(2,4,6-trimethylphenyl)-2,2'-biphenol and phosphorus trichloride to yield the corresponding dichloro-bisphosphite PIV-TMP-PCl$_2$, which was reacted with 3,5-dibromosalicylic acid to yield phosoxophite FF. Purified yield: 79%. Three diastereomers were observed in $^{31}$P {$^1$H} NMR spectrum in the ratio close to 78:13:9. $^{31}$P {$^1$H} NMR (121.66 MHz, CDCl$_3$, δ): diastereomer 1 (78%): 120.67 and 139.37 ppm (d, $J_{P-P}$=3.3 Hz); diastereomer 2 (13%): 114.80 and 138.91 ppm (d, $J_{P-P}$=6.8 Hz); diastereomer 3 (9%): 121.62 and 140.54 ppm(s).

Phosoxophite GG was prepared by reacting the dichloro-bisphosphite PIV-TMP-PCl$_2$, prepared hereinabove, with 3,5-di(isopropyl)salicylic acid. Purified yield: 78%. Three diastereomers were observed in $^{31}$P {$^1$H} NMR spectrum in the ratio close to 73:18:9. $^{31}$P {$^1$H} NMR (121.66 MHz, CDCl$_3$, δ): diastereomer 1 (73%): 118.80 and 139.29 ppm (d, $J_{P-P}$=4.4 Hz); diastereomer 2 (18%): 115.04 and 139.96 ppm (d, $J_{P-P}$=9.4 Hz); diastereomer 3 (9%): 121.01 and 140.79 ppm(s).

The phosoxophite compositions were evaluated as ligands in the hydroformylation of 3-pentenol in a Parr pressurized reactor. The general procedure for each reaction was as follows. The reactor was cleaned, assembled, evacuated, placed under nitrogen, and then leak tested with nitrogen at the reaction pressure. A catalyst solution containing the phosoxophite ligand, $Rh(CO)_2$acac, and a base (either N,N-dimethylaniline or N,N-diisopropylethylamine) was prepared in tetrahydrofuran (5 g) and tetraglyme (20 g). An olefin-containing solution was prepared containing 3-pentenol and an internal standard. An initial sample was taken from the 3-pentenol solution (0.10 ml) and diluted with about 0.2 ml tetrahydrofuran and about 0.8 ml tetraglyme for gas chromatographic (GC) analysis. Under nitrogen, the catalyst solution was added into the reactor, and the olefin solution was added into an olefin-injection cylinder attached to the reactor. Both solutions were purged three times with carbon monoxide and hydrogen at the reaction partial pressures. The reactor was then sealed, stirred and heated under carbon monoxide and hydrogen at partial pressures 5 psia below the designated reaction partial pressures. When the reaction solution reached target temperature, the olefin solution was forced into the reactor with carbon monoxide and hydrogen at partial pressures 10 psi above the designated reaction partial pressures. Immediately after the addition of olefin, the pressure in the reactor was adjusted to the designated partial pressures of carbon monoxide and hydrogen and designated total reaction pressure. The reactor was then fed with a 1:1 volume ratio of $H_2$/CO synthesis gas at the reaction pressure. Two to four samples were taken during the course of the reaction for GC analysis. Isoprene was added to each GC sample to deactivate the rhodium catalyst. A $^{31}P$ NMR sample was taken at the end of the reaction. The reaction conditions and results are shown in Table 1.

EXAMPLE 4

The phosoxophite compositions DD and Z were prepared in a manner analogous to the synthesis of Example 2. The specific reagents used were the following.

Phosoxophite DD was prepared by reacting 3,3'-di(trimethylsilyl)-5,5'-di-t-butyl-2,2'-biphenol with phosphorus trichloride to prepare the corresponding phosphoromonochloridite TMS-PCl, which was reacted with 3,3'-trinethylsilyl-5,5'-di-t-butyl-2,2'-biphenol and phosphorus trichloride to yield the corresponding dichloro-bisphosphite TMS-TMS-PCl$_2$, which was reacted with 3,5-di(isopropyl) salicylic acid to yield the phosoxophite ligand DD. Purified yield: 83%. Four diastereomers were observed in $^{31}P\{^1H\}$ NMR spectum in the ratio close to 62:30:6:2. $^{31}P\{^1H\}$ NMR (121.66 MHz, THF, δ): diastereomer 1 (62%): 120.39 and 143.14 ppm(s); diastereomer 2 (30%): 117.17 and 143.90 ppm(s); diastereomer 3 (6%): 121.81 and 143.34 ppm(s); diastereomer 4 (2%): 116.32 and 141.65 (s).

Phosoxophite Z was prepared by reacting 3,3'-di(trimethylsilyl)-5,5'-di-t-butyl-2,2'-biphenol with phosphorus trichloride to prepare the corresponding phosphoromonochloridite TMS-PCl, which was reacted with 3,3'-di-t-butyl-5,5'-di(2,4,6-trimethylphenyl)-2,2'-biphenol and phosphorus trichloride to yield the corresponding dichloro-bisphosphite, which was reacted with 3,5-di(isopropyl)salicylic acid to yield the phosoxophite ligand Z. Purified yield: 83%. Three diastereomers were observed in $^{31}P\{^1H\}$ NMR spectrum in the ratio close to 84:14:2. $^{31}P\{^1H\}$ NMR (121.66 MHz, CDCl$_3$, δ): diastereomer 1 (84%): 114.94 and 140.32 ppm (d, $J_{P-P}$=3.2 Hz); diastereomer 2 (14%): 110.68 and 139.00 ppm (d, $J_{P-P}$=9.6 Hz); diastereomer 3 (2%): 116.39 and 140.96 ppm(s).

TABLE 1

Hydroformylation of 3-Pentenol Using Rh(Phosoxophite) Catalyst

| Phosoxophite | [Rh] ppm | CO/H$_2$ psia | L/Rh Mol ratio | Temp °C. | Olefin Conv[1] mol % | 6HH[2] mol % | N:I[3] mol | Rate[4] M/h |
|---|---|---|---|---|---|---|---|---|
| M | 303 | 15/15 | 2.4 | 53 | 98 | 87 | 14 | 1.2 (19%) |
| N | 301 | 15/15 | 2.4 | 60 | 100 | 78 | 9.6 | 1.2 (28%) |
| O | 300 | 33/67 | 3 | 75 | 99 | 74 | 6.7 | 0.94 (29%) |
| Q | 151 | 15/15 | 3.0 | 53 | 100 | 89 | 28 | 0.44 (45%) |
| R | 315 | 15/15 | 2.4 | 60 | 100 | 79 | 15 | 1.02 (26%) |
| FF | 308 | 16/16 | 2.4 | 52 | 100 | 85 | 38 | 0.59 (23%) |
| GG | 305 | 26/32 | 2.4 | 63 | 97 | 80 | 34 | 0.53 (15%) |

[1]Olefin Conv (mol %) = mole percentage of olefin feed converted to all products.
[2]6HH (mol %) = yield of 6-hydroxyhexanal, as mole percentage based on initial olefin feed.
[3]N:I (mol) = molar ratio of normal product to iso products
[4]Rate (M/h) = average initial reaction rate in g-moles hydroformylation product formed per liter per hour (at specified conversion).

The data in Table 1 show that the phosoxophite compositions of this invention can be suitably employed as ligands in Group VIII transition metal complex catalysts that are active in the hydroformylation of internal olefins. The catalyst, formed in situ under reaction conditions, achieved high conversion of the internal C$_5$ olefin, high selectivity to the normal C$_6$ aldehyde product with high isomerization selectivity, and an acceptable reaction rate.

The compositions DD and Z were tested in the hydroformylation of 1-octene and 2-octene by following procedures similar to those described in Example 3. The reactions were carried out using 300 ppm rhodium, 2/1 ligand to rhodium mole ratio in tetrahydrofuran (about 10 g) and tetraglyme (about 10 g) under 50 psia carbon monoxide and 50 psia of hydrogen gas. Other reaction conditions and the results are shown in Table 3 hereinbelow.

TABLE 2

Hydroformylation of Octenes using Rh(Phosoxophite) Catalyst[1]

| Phosoxophite | Substrate | Temp. °C. | Olefin Conv[2] mol % | Sel. Linear[3] mol % | Sel. Br[3] mol % | Sel. Isom.[3] mol % | Sel. Octane[3] mol % | Rate[4] M/hr (% Conv) |
|---|---|---|---|---|---|---|---|---|
| DD | 1-Octene | 45 | 100 | 93.6 | 1.9 | 4.5. | .4 | 1.37 (22%) |
|  | 2-Octene | 70 | 96 | 76.9 | 6.1 | 17.1 | 1.2 | 0.51 (18%) |
| Z | 1-Octene | 45 | 100 | 92.9 | 0.8 | 5.7 | 0.5 | 2.05 (23%) |
|  | 2-Octene | 70 | 67 | 88.1 | 3.4 | 8.4 | .1 | 0.18 (50%) |

[1]Rxn. conditions: 300 ppm Rh, 2/1 ligand to rhodium mole ratio, 50 psia CO, 50 psia $H_2$.
[2]Olefin Conv (mol %) = mole percentage of olefin feed converted to all products.
[3]Selectivities to products: linear C9 product (1-nonanal), branched C9 products (Br), isomerized C8 olefin (Isom), and octane.
[4]Rate (M/h) = average initial reaction rate in units of g-mol hydroformylation product formed per liter per hour (at specified conversion).

The data in Table 2 show that phosoxophite compositions DD and Z of this invention are suitably employed as ligands in Group VIII transition metal complexes that are used in the hydroformylation of internal and terminal olefins. The catalysts exhibited good activity and good selectivity to the linear product. Little isomerization to internal olefins and little hydrogenation to saturated products were found.

EXAMPLE 5

The phosoxophite composition AA, shown hereinbefore, was synthesized in a manner analogous to that described in Example 2. Specifically, 3,3'-trimethylsilyl-5,5'-di-t-butyl-2, 2'-biphenol was reacted with phosphorus trichloride to yield the corresponding TMS-PCl phosphoromonochloridite, which was reacted with 3,3'-di t-butyl-5,5'-di(2,4,6-trimethylphenyl)-2,2'-biphenol and phosphorus trichloride to yield the corresponding dichloro-bisphosphite, which was reacted with 3,5-dibromosalicylic acid to yield the phosoxophite composition AA. Purified yield: 83%. Two diastereomers were observed in $^{31}P\{^1H\}$ NMR spectrum in the ratio close to 87:13. $^{31}P\{^1H\}$ NMR (121.66 MHz, CDCl$_3$, δ): diastereomer 1 (87%): 119.88 and 145.15 ppm (d, $J_{P-P}$=4.5 Hz); diastereomer 2 (13%): 115.00 and 143.49 ppm (d, $J_{P-P}$=8.5 Hz.

Composition AA was evaluated as a ligand in rhodium complex catalyzed hydroformylation reactions of styrene, methyl acrylate and vinyl acetate, using procedures similar to those described in Example 3. The reactions were carried out at 60° C. using 1.5/1 ligand to rhodium mole ratio in tetrahydrofuran (about 10 g) and tetraglyme (about 10 g) under 15 psia carbon monoxide and 15 psia hydrogen gas. Other reaction conditions and the results are shown in Table 3 below.

TABLE 3

Hydroformylation (HF) Using Rh(Phosoxophite AA) Complex Catalyst[1]

| Phosoxophite | Substrate | [Rh] ppm | Conv. %[2] | Linear Prod. %[3] | Br Prod. % | Hydrog % | N:I | Rate[a] M/hr (% Conv)[4] |
|---|---|---|---|---|---|---|---|---|
| AA | Styrene | 250 | 99 | 91.6 | 6.4 | 1.9 | 14 | 2.03 (23%) |
|  | Methyl acrylate | 100 | 100 | 91.1 | 0.9 | 8.0 | 101 | 2.23 (22%) |
|  | Vinyl acetate | 100 | 96 | 10.2 | 88.2 | 1.6 | 0.12 | 2.58 (28%) |

[1]Rxn. conditions: 1.5/1 ligand to rhodium mole ratio, 60° C., 15 psia CO, 15 psia $H_2$.
[2]Olefin Conv (mol %) = mole percentage of olefin feed converted to all products.
[3]Selectivities to products: linear HF product, branched (Br) HF product, hydrogenated (Hydrog) product.
[4]Rate (M/h) = average initial reaction rate in units of g-mols hydroformylation product formed per liter per hour (at specified conversion).

The data in Table 3 show that phosoxophite composition AA can be suitably employed as a ligand in rhodium complex catalyzed hydroformylation reactions of substituted olefins, such as styrene, methyl acrylate, and vinyl acetate, which, particularly styrene and vinyl acetate have the tendency of producing more branched aldehydes. The catalyst achieved a high conversion of olefin, surprisingly high selectivity to linear hydroformylation product from styrene, and an advantageously low hydrogenation activity.

The invention claimed is:

1. A phosoxophite composition selected from the group consisting of the following formulas:

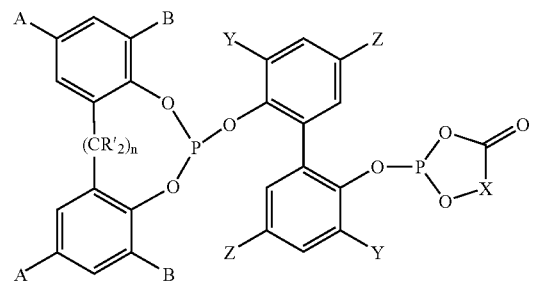

(IIa)

and

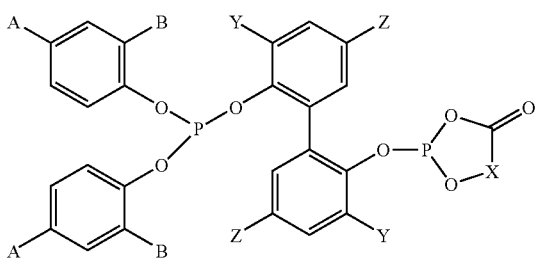

(IIb)

wherein each A and Z is independently selected from the group consisting of hydrogen, halogen, monovalent hydrocarbyl radicals, and tri(hydrocarbyl)silyl radicals; each B and Y is independently selected from aryl radicals, tertiary alkyl radicals, and tri(hydrocarbyl)silyl radicals, with the proviso that at least one B or at least one Y is a tri(hydrocarbyl)silyl radical; each $R^1$ is independently selected from the group consisting of hydrogen, monovalent alkyl, and monovalent aryl radicals; n is an integer from 0 to 2; and X is selected from the group consisting of alkyl and aryl diradicals and substituted derivatives thereof.

2. The composition of claim 1 wherein each A and Z is independently selected from the group consisting of hydrogen, halo, alkyl, aryl, alkaryl, aralkyl, alicyclic, alkoxy, aryloxy, hydrocarbyl carbonyl, hydrocarbyl carboxy, and tri(hydrocarbyl)silyl radicals, the hydrocarbyl or tri(hydrocarbyl)silyl radicals having from 1 to about 20 carbon atoms; each B and Y is independently selected from aryl radicals not having substituents on ortho positions, tertiary alkyl radicals, and tri(hydrocarbyl)silyl radicals, the Y radicals having from 3 to about 30 carbon atoms.

3. The composition of claim 1 wherein each A is independently selected from hydrogen, chloro, bromo, iodo, methyl, ethyl, tertiary butyl, isoamyl, tertiary amyl, tertiary octyl, methoxy, acetyl [CH$_3$C(O)—], propionyl [CH$_3$CH$_2$C(O)—] and trimethylacetoxy [(CH$_3$)$_3$C—C(O)O—] radicals; and each Z is independently selected from tertiary butyl, tertiary amyl, tertiary octyl, tri(methyl)silyl, tri(ethyl)silyl, xylyls, dimethylphenyls, diethylphenyls, trimethylphenyls, and trimethylacetoxy radicals.

4. The composition of claim 1 wherein each B is independently selected from tertiary butyl, trimethylsilyl, phenyl, 3,5-dimethylphenyl, and 3,4,5-trimethylphenyl radicals; and each Y is independently selected from tertiary butyl and trimethylsilyl radicals.

5. The composition of claim 1 wherein both B's are tri(hydrocarbyl)silyl radicals or both Y's are tri(hydrocarbyl)silyl radicals.

6. The composition of claim 1 wherein X is an allyl or aryl diradical selected from the group consisting of methylene (—CH$_2$—), ethylene (—CH$_2$CH$_2$—), 1,3-propylene (—CH$_2$CH$_2$CH$_2$—), 1,2-phenylene (—C$_6$H$_4$—), 1,2-naphthylene (—C$_{10}$H$_6$—), 2,3-naphthylene (—C$_{10}$H$_6$), 3,5-dichloro-1,2-phenylene, 3,5-dibromo-1,2-phenylene, 3-iodo-5-methyl-1,2-phenylene, 3,5-diisopropyl-1,2-phenylene, 3,5,6-trichloro-1,2-phenylene, 3-phenyl-1,2-phenylene, 1,1-diethyl-1,1-methylene, 1,1-cyclohexylidene, 1,1-cycloheptylidene, and 3-isopropyl-6-methyl-1,2-phenylene.

7. The composition of claim 1 wherein each $R^1$ is selected from the group consisting of hydrogen, $C_{1-6}$ alkyl, and phenyl radicals.

8. The composition IIa of claim 1, wherein n is 0, and the composition is represented by the formula:

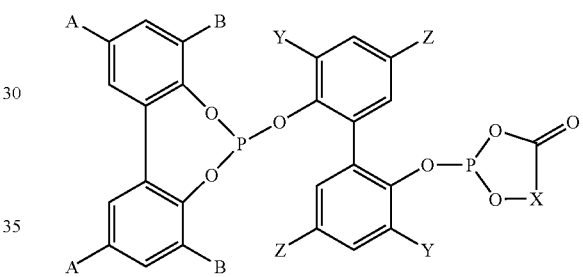

wherein A, B, Y, and Z are as defined in claim 1.

9. A phosoxophite composition represented by the following formula:

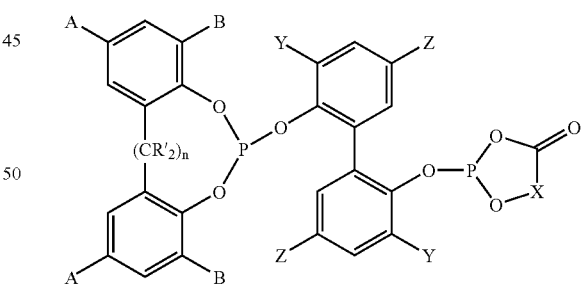

wherein each A and Z is independently selected from the group consisting of hydrogen, halogen, monovalent hydrocarbyl radicals, and tri(hydrocarbyl)silyl radicals; each B and Y is independently selected from aryl radicals, tertiary alkyl radicals, and tri(hydrocarbyl)silyl radicals, with the proviso that at least one B or at least one Y is a tri(hydrocarbyl)silyl radical; n is 0; such composition being selected from the group consisting of the following formulas, wherein X is an alkyl or aryl diradical of from 1 to 3 carbon atoms (X optionally, further comprising one or more substituents of from 1 to 20 carbon atoms):

-continued
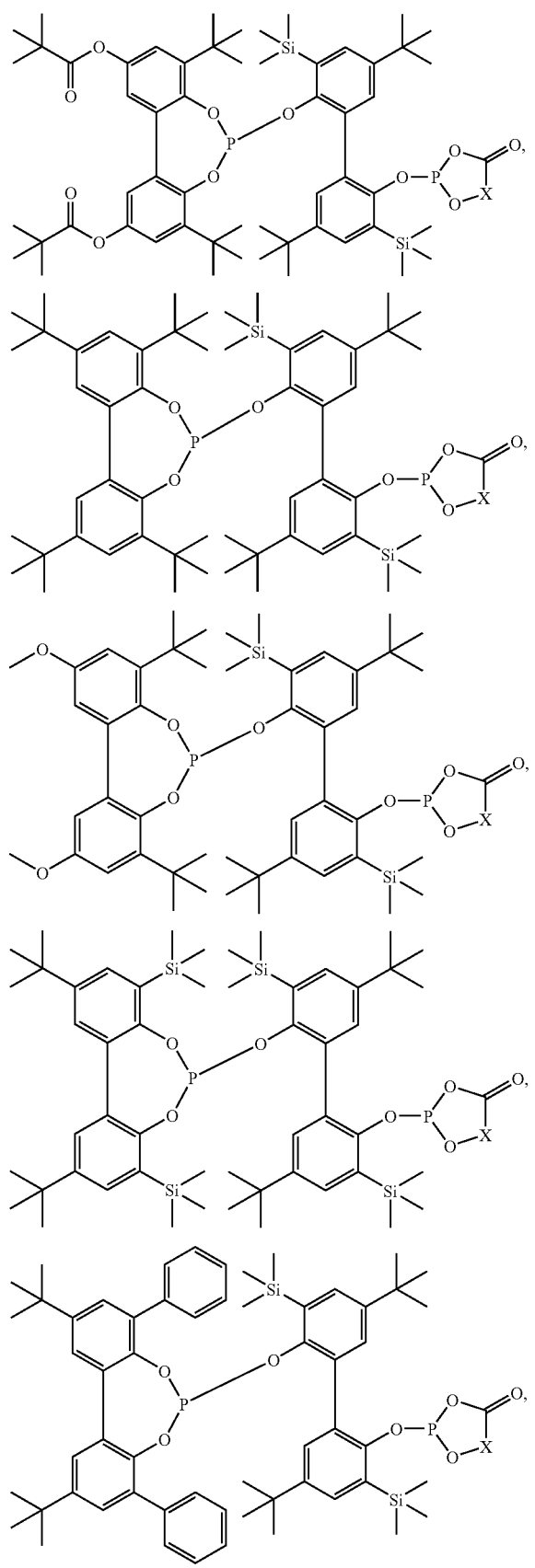
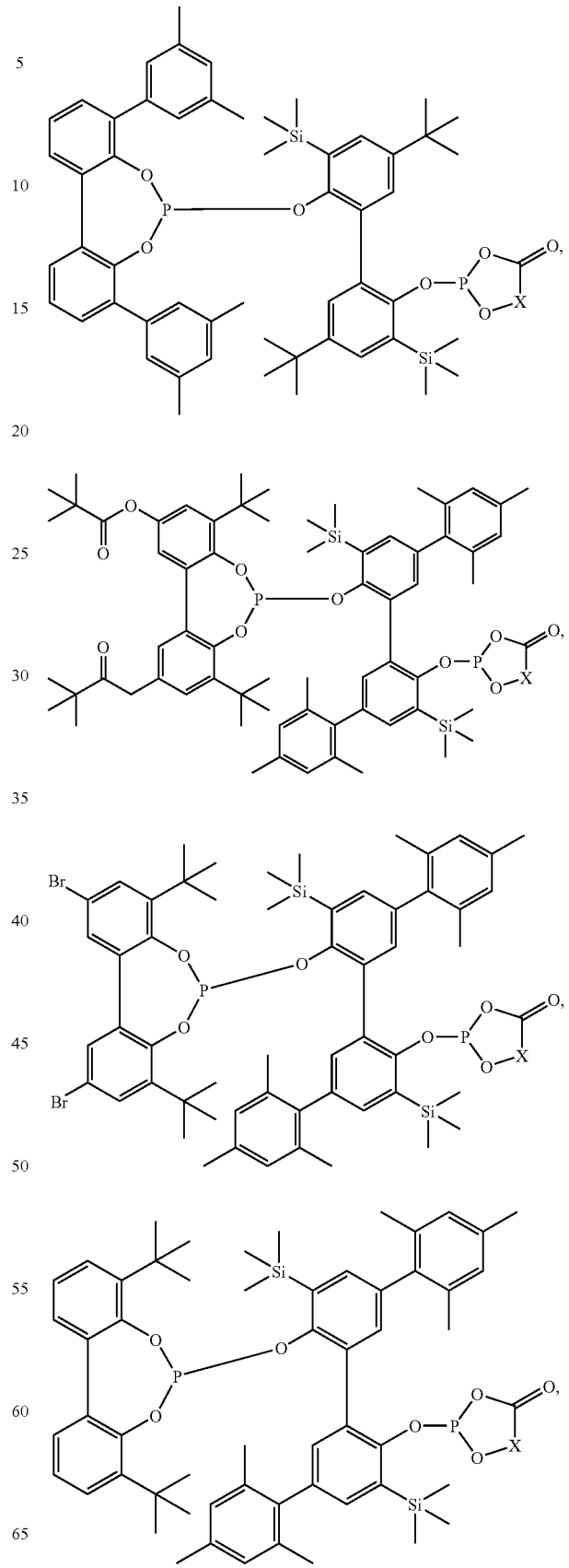

-continued

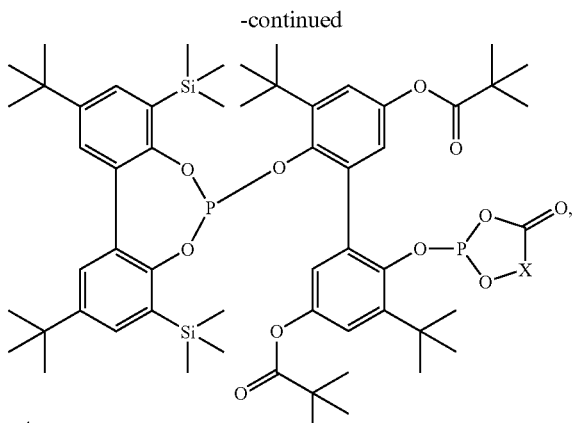

and

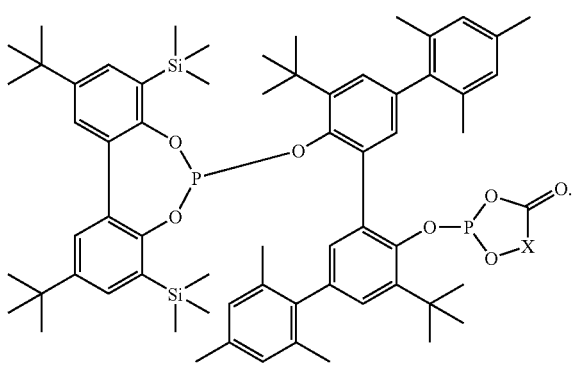

10. A phosoxophite composition represented by the following formula:

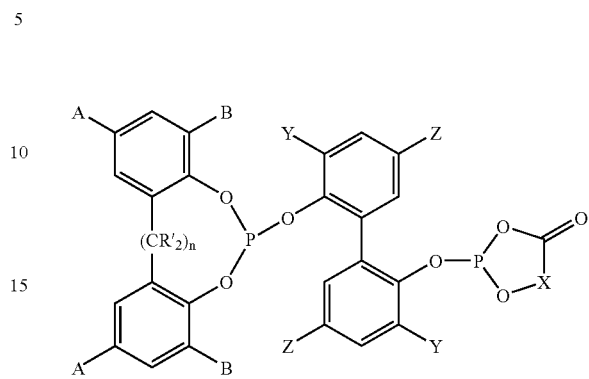

wherein each A and Z is independently selected from the group consisting of hydrogen, halogen, monovalent hydrocarbyl radicals, and tri(hydrocarbyl)silyl radicals; each B and Y is independently selected from aryl radicals, tertiary alkyl radicals, and tri(hydrocarbyl)silyl radicals, with the proviso that at least one B or at least one Y is a tri(hydrocarbyl)silyl radical; and n is 0; such composition being selected from the group consisting of:

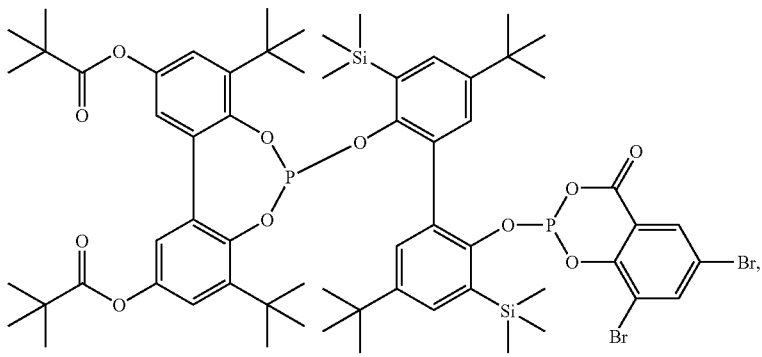

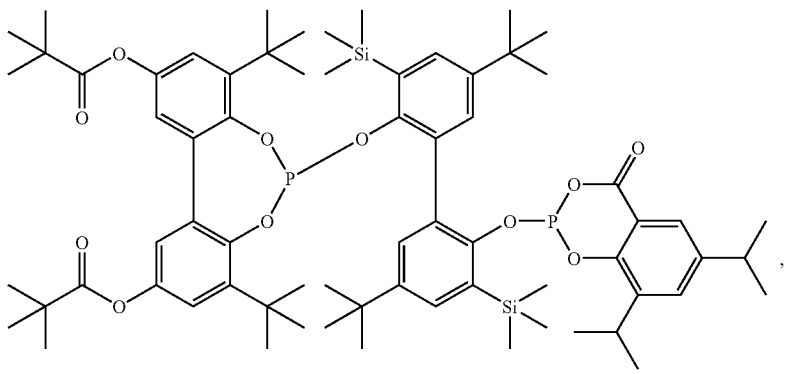

-continued
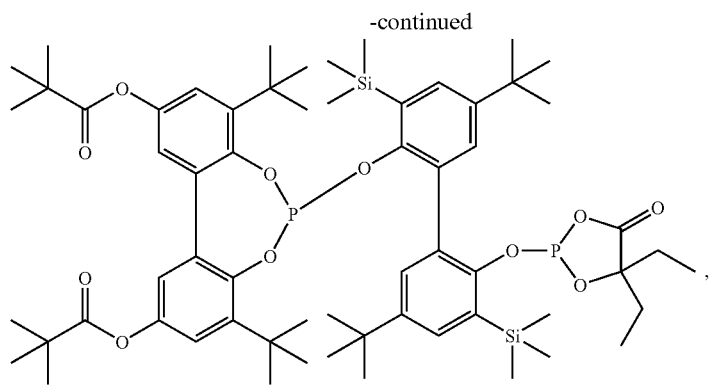
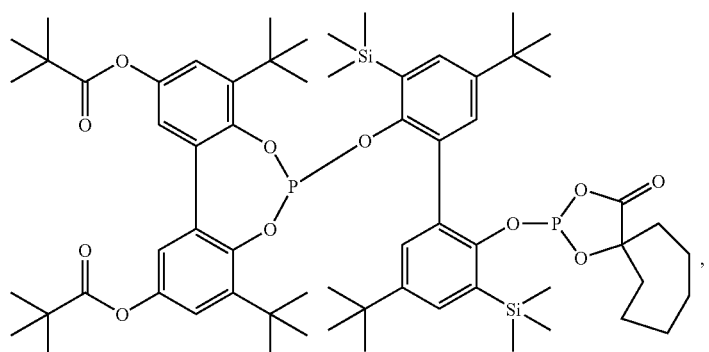
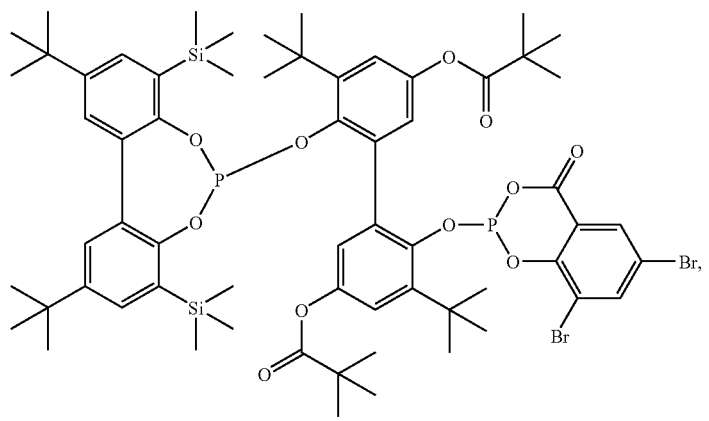
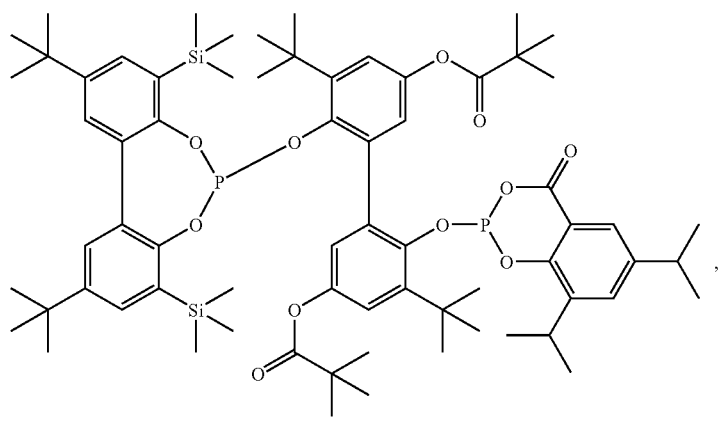

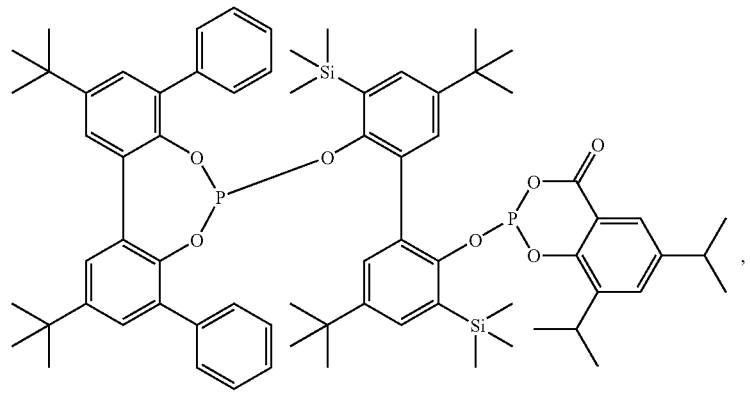
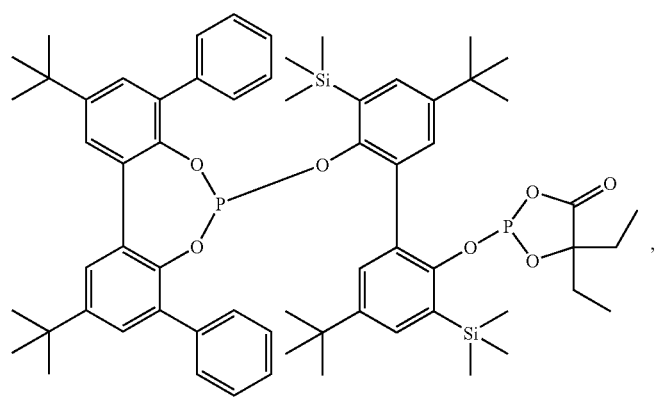
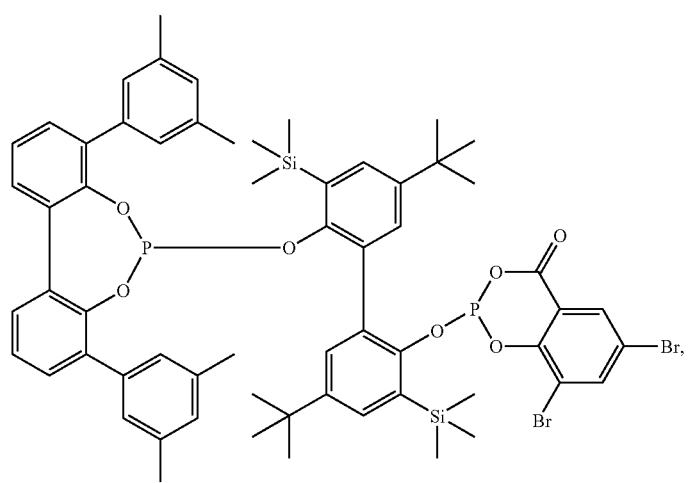

-continued
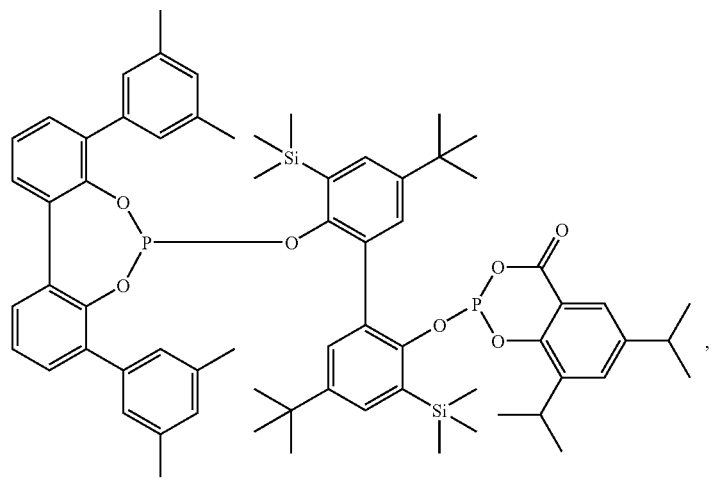
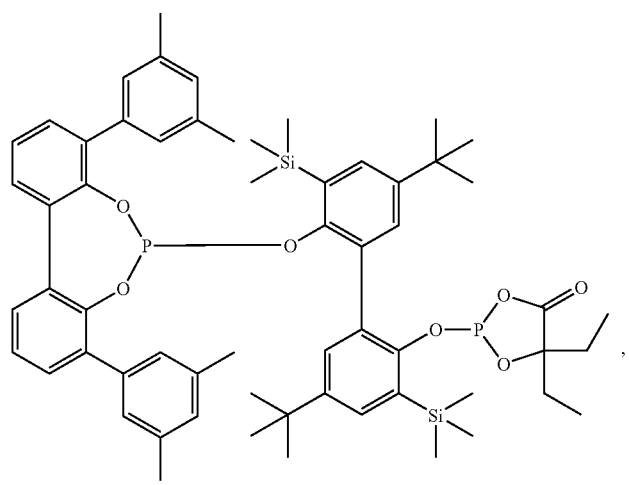
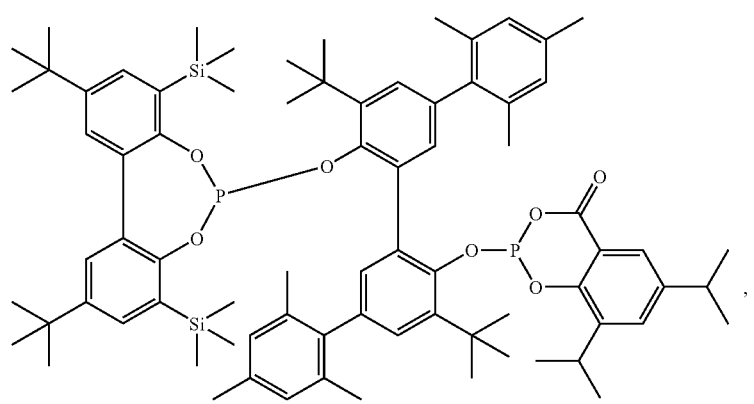

-continued
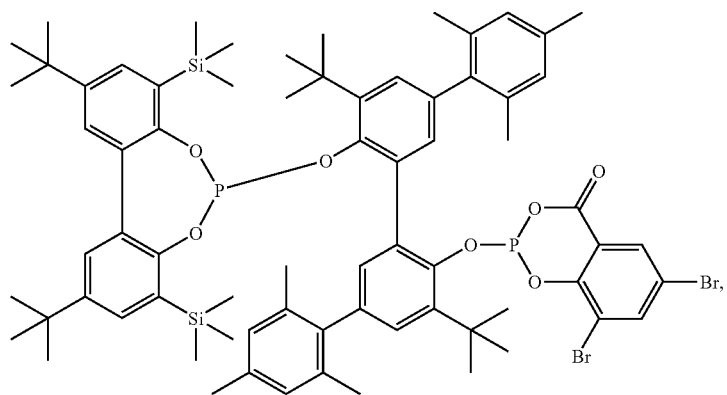
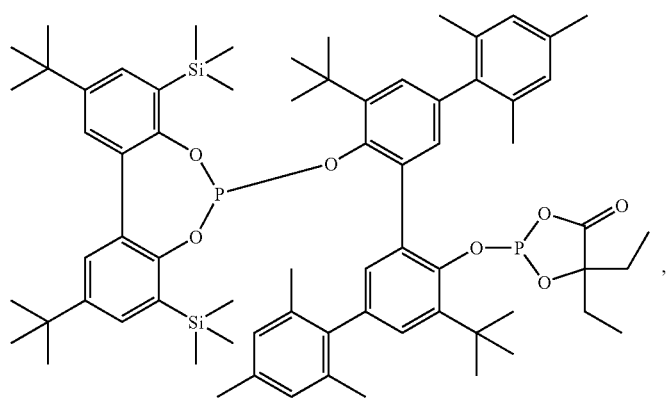
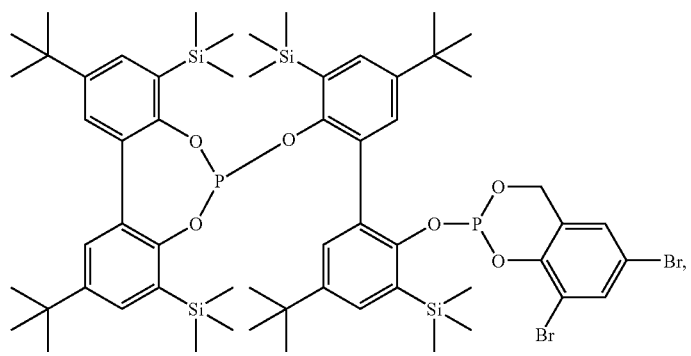
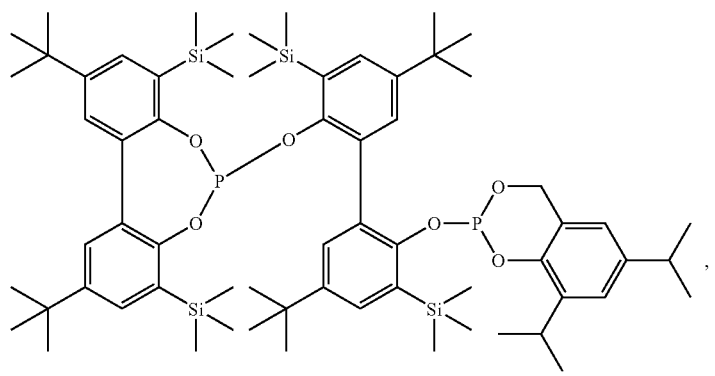

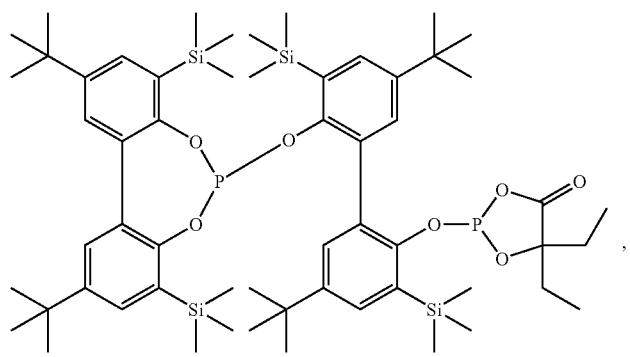
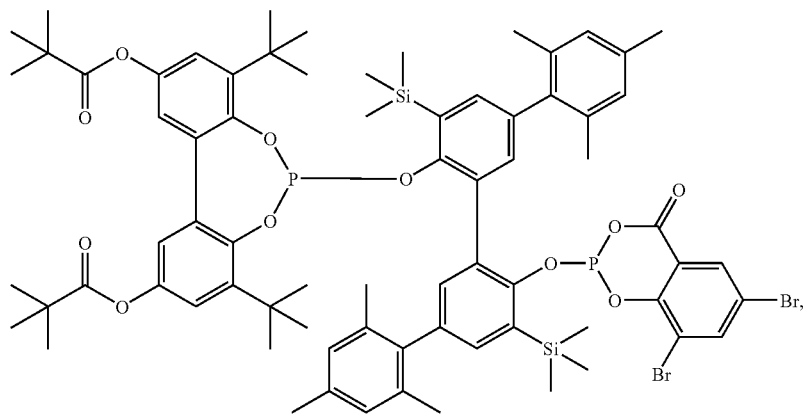
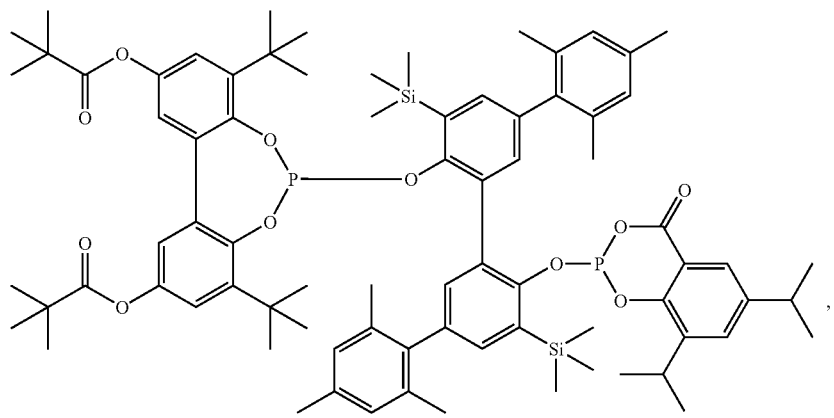
and
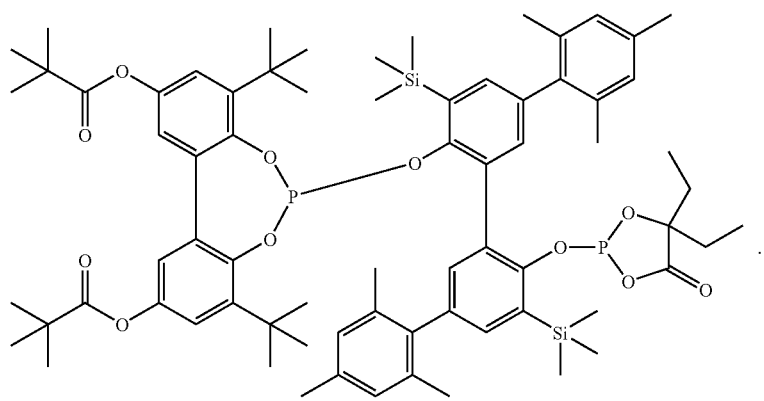

11. A process of preparing a phosoxophite composition having the formula:

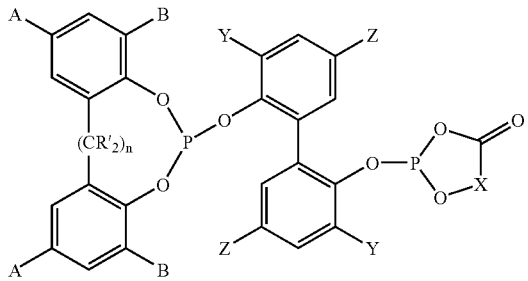

wherein each A and Z is independently selected from the group consisting of hydrogen, halogen, monovalent hydrocarbyl radicals, and tri(hydrocarbyl)silyl radicals; each B and Y is independently selected from aryl radicals, tertiary alkyl radicals, and tri(hydrocarbyl)silyl radicals, with the proviso that at least one B or at least one Y is a tri(hydrocarbyl)silyl radical; each $R^1$ is independently selected from the group consisting of hydrogen, monovalent alkyl, and monovalent aryl radicals; n is an integer from 0 to 2; and X is selected from the group consisting of alkyl and aryl diradicals and substituted derivatives thereof; the process comprising contacting a dichloro-bisphosphite composition represented by the following formula:

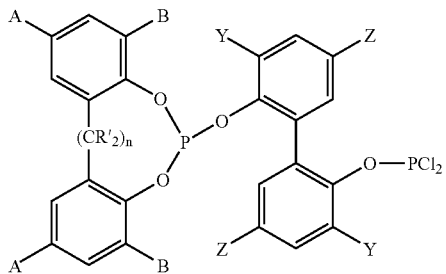

wherein A, B, $R^1$, n, Y, and Z are as defined hereinabove, with a hydroxyacid represented by the following formula:

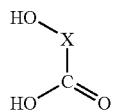

wherein X is as defined hereinabove, the contacting being conducted in the presence of a base and under reaction conditions sufficient to prepare the phosoxophite composition.

12. The process of claim 11 wherein the molar ratio of dichloro-bisphosphite compound to hydroxy acid is greater than about 0.7/1 and less than about 1.3/1.

13. The process of claim 11 wherein the base is selected from trialkyl amines and N-heterocycles.

14. The process of claim 11 wherein the molar ratio of base to dichloro-bisphosphite is greater than about 2.2/1, but less than about 2.7/1.

15. The process of claim 11 wherein the temperature is greater than about −35° C. and less than about 60° C.

16. A transition metal complex catalyst or complex catalyst precursor comprising a Group VIII transition metal bonded to at least one molecule of phosoxophite ligand selected from the formulas of claim 1, optionally, further bonded to carbon monoxide, hydrogen, or both carbon monoxide and hydrogen.

17. The composition of claim 16 wherein the Group VIII transition metal is selected from ruthenium, rhodium, cobalt, and iridium.

18. The composition of claim 16 wherein the Group VIII transition metal is rhodium.

19. A solution comprising an organic solvent, free phosoxophite ligand, and a transition metal complex catalyst or complex catalyst precursor composition comprising a Group VIII transition metal bonded to at least one molecule of phosoxophite ligand, wherein the free and bonded phosoxophite ligands are selected from the formulas of claim 1.

20. The solution of claim 19 wherein the Group VIII transition metal is selected from the group consisting of ruthenium, rhodium, cobalt, and iridium.

21. The solution of claim 19 wherein the Group VIII transition metal is rhodium.

22. A carbonylation process comprising contacting an organic compound capable of being carbonylated with carbon monoxide in the presence of a transition metal complex catalyst comprising a Group VIII transition metal bonded to at least one molecule of phosoxophite ligand, optionally, in the presence of free phosoxophite ligand; wherein the bonded and free phosoxophite ligands are independently selected from the formulas shown in claim 1, the contacting being conducted under carbonylation conditions sufficient to prepare the corresponding carbonylated organic compound.

23. The carbonylation process of claim 22 wherein the carbonylation comprises a simple carbonylation, hydroformylation, hydroacylation, hydrocyanation, hydroamidation, hydroesterification, and hydrocarboxylation.

24. The carbonylation process of claim 22 wherein the Group VIII transition metal is selected from ruthenium, rhodium, cobalt, and iridium.

25. The carbonylation process of claim 22 wherein the process comprises a hydroformylation process wherein an olefinically unsaturated aliphatic hydrocarbon is contacted with carbon monoxide in the presence of hydrogen.

26. The hydroformylation process of claim 25 wherein the olefinically unsaturated aliphatic hydrocarbon contains from 2 to 60 carbon atoms and one or more unsaturated groups.

27. The carbonylation process of claim 25 wherein the olefinically unsaturated aliphatic hydrocarbon is selected from the group consisting of alpha olefins, internal olefins, alkyl alkenoates, alkenyl alkanoates, alkenyl alkyl ethers, and alkenols.

28. The carbonylation process of claim 25 wherein the olefinically unsaturated aliphatic hydrocarbon is selected from the group consisting of ethylene, propylene, 1-butene, 1-pentene, 1-hexene, 1-octene, 1-decene, 1-dodecene, 1-octadecene, 2-butene, 2-methyl propene (isobutylene), isoamylene, 2-pentene, 2-hexene, 3-hexene, 2-heptene, cyclohexene, propylene dimers, propylene trimers, propylene tetramers, 2-ethylhexene, styrene, 3-phenyl-1-propene, butadiene, 1,3-cyclohexadiene, 1,4-cyclohexadiene, 1,7-octadiene, 3-cyclohexyl-1-butene, allyl alcohol, hex-1-en-4-ol, oct-1-ene-4-ol, vinyl acetate, allyl acetate, 3-butenyl acetate, vinyl propionate, 1-vinyl-3-cyclohexene, allyl propionate, allyl butyrate, methyl methacrylate, 3-butenyl acetate, vinyl ether, vinyl methyl ether, allyl ethyl. ether, n-propyl-7- octenoate, methyl 1-decenoate, 3-butenenitrile, 5-hexenamide, methyl oleate, soybean oil and castor oil.

29. The carbonylation process of claim 22 wherein the carbonylation process is conducted in the presence of a solvent selected from the group consisting of saturated hydrocarbons, aromatic hydrocarbons, ethers, aldehydes, ketones, nitriles, and aldehyde condensation products.

30. The carbonylation process of claim 22 wherein the process is conducted in the presence of free phosoxophite ligand selected from the phosoxophite ligands represented by the formulas in claim 1.

31. The carbonylation process of claim 22 wherein the molar ratio of phosoxophite ligand to Group VIII transition metal is greater than about 3/1 and less than about 100/1.

32. The carbonylation process of claim 22 wherein the carbonylation process temperature is greater than about 30° C. and less than about 200° C.

33. The carbonylation process of claim 24 wherein the carbonylation process total pressure is greater than about 1 psia (7kPa) and less than about 10,000 psia (68,948kPa).

34. The carbonylation process of claim 22 wherein the carbon monoxide partial pressure is greater than about 1 psia (7kPa) and less than about 1,000 psia (6,895kPa); and wherein in a hydroformylation process, the hydrogen partial pressure is greater than about 5 psia (35psia) and less than about 1,000 psia (6,895kPa).

35. The carbonylation process of claim 34 wherein the $H_2$/CO molar ratio of gaseous hydrogen to carbon monoxide is greater than about 1/10 and less than about 100/1.

36. The carbonylation process of claim 25, wherein the process is a hydroformylation process, and wherein the process temperature is greater than about 30° C. and less than about 150° C.

37. The carbonylation process of claim 22 wherein the concentration of transition metal is greater than about 10 ppm and less than about 1,000 ppm.

38. The composition of claim 16 wherein the phosoxophite ligand is selected from the group consisting of:

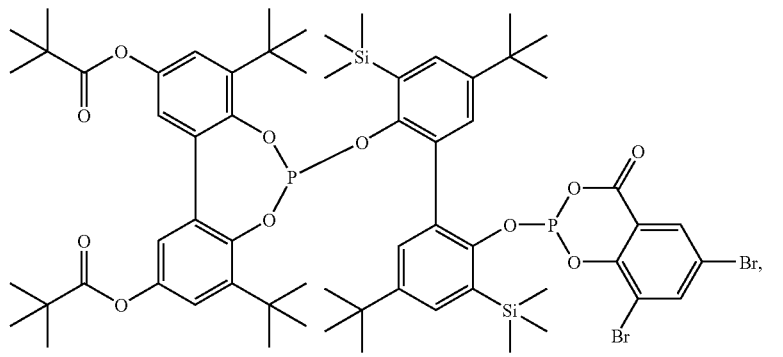

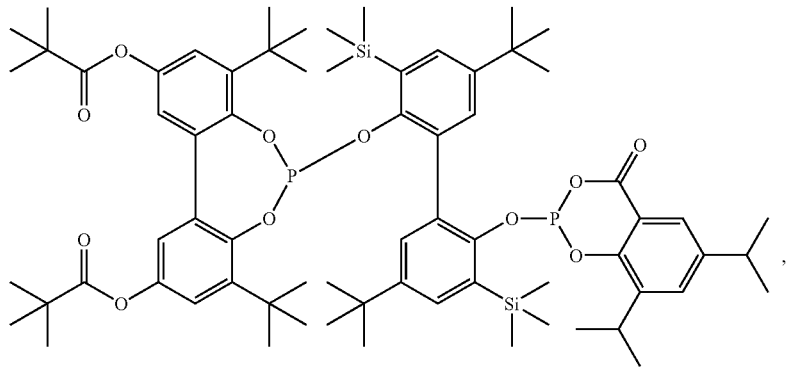

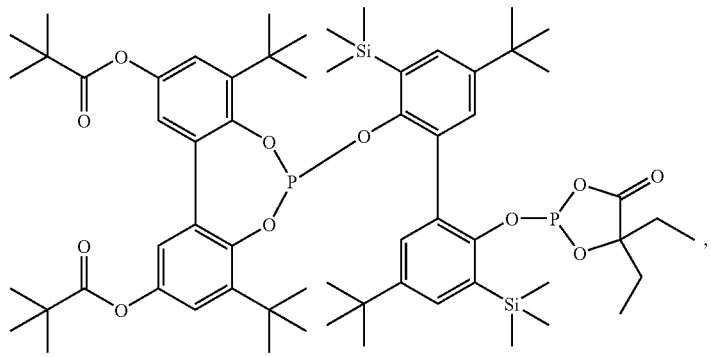

-continued
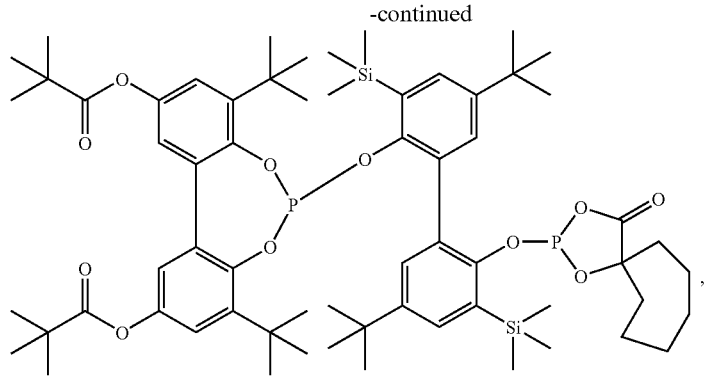
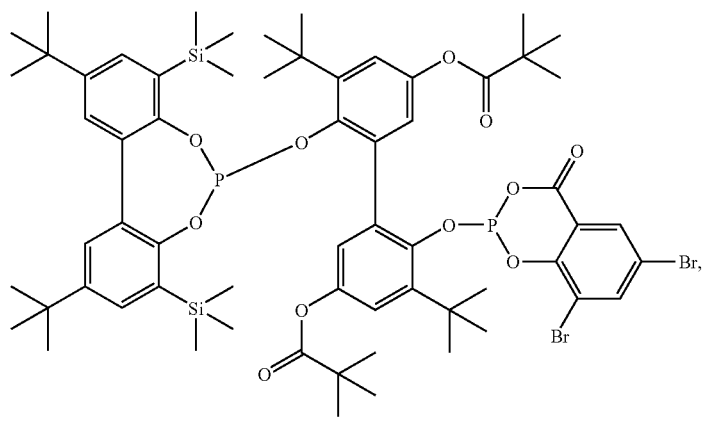
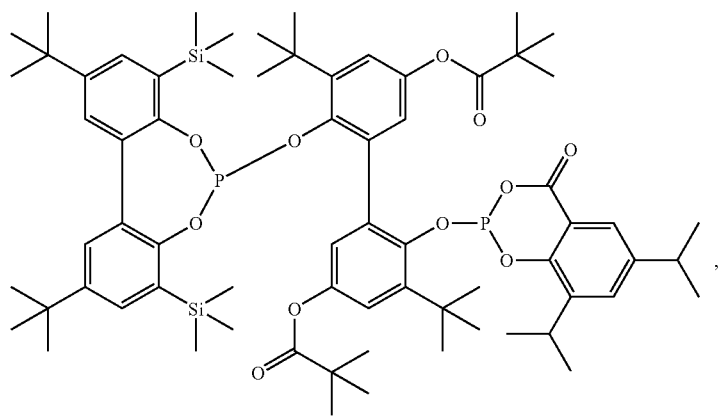
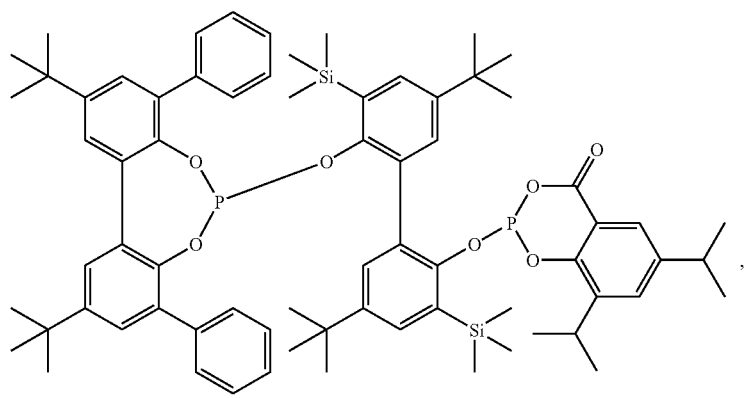

-continued
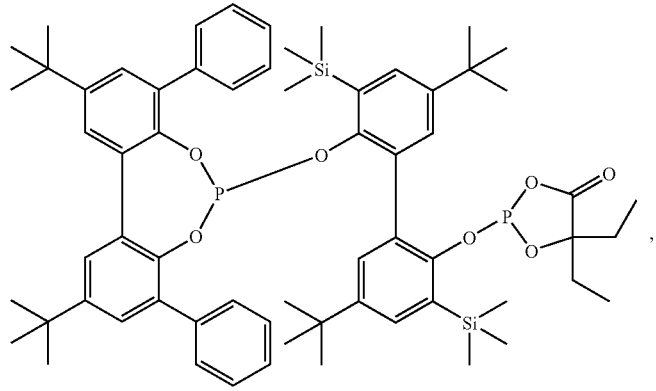
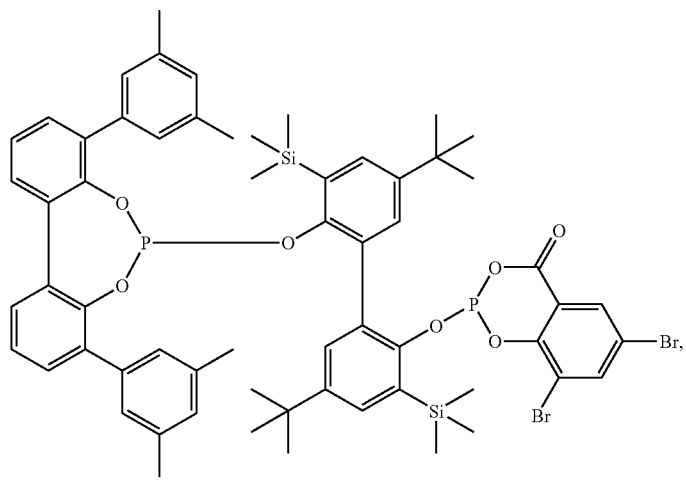
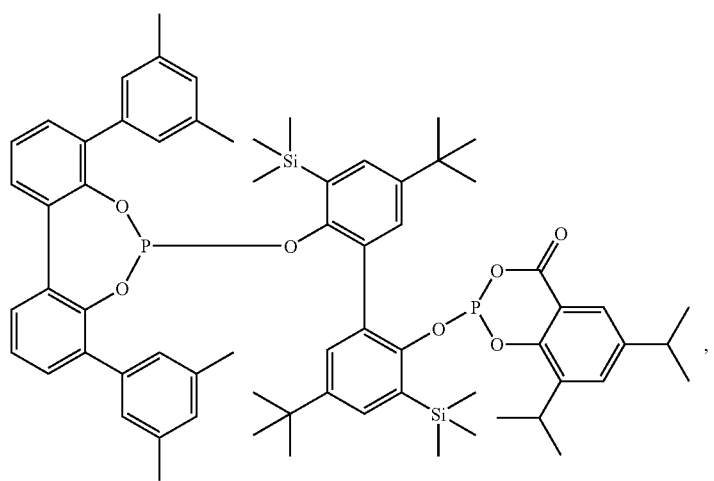

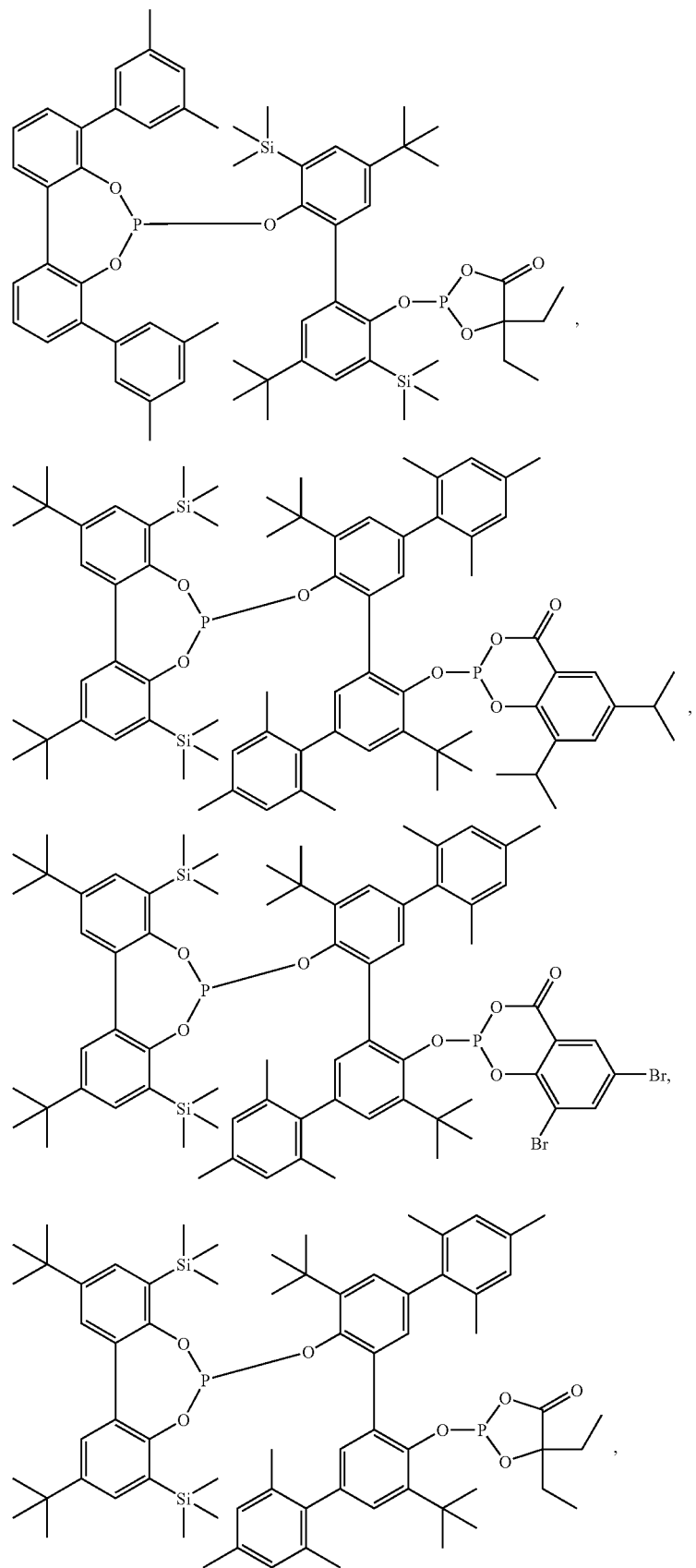

-continued
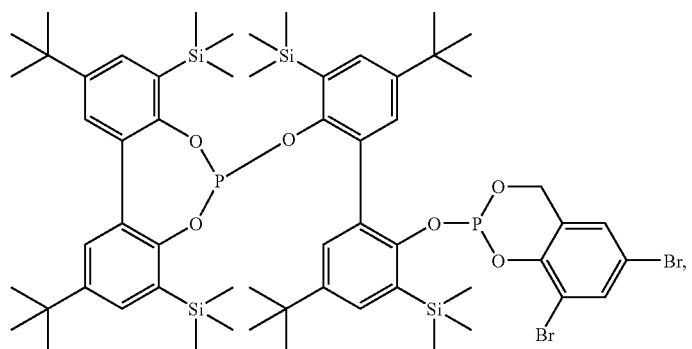
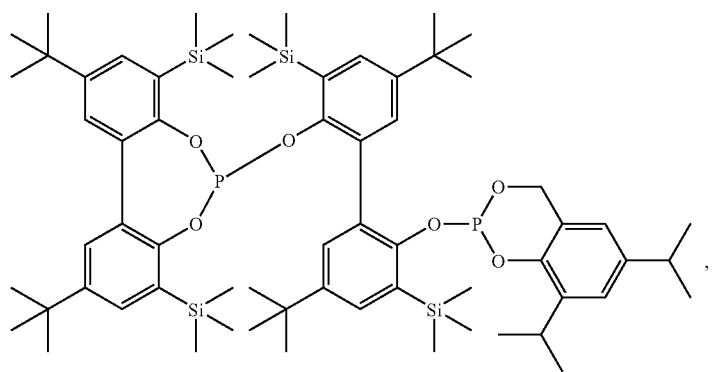
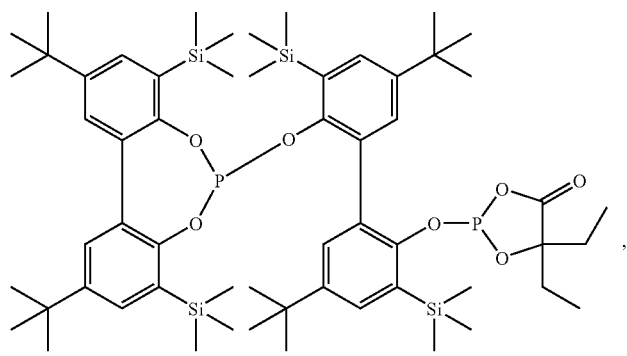
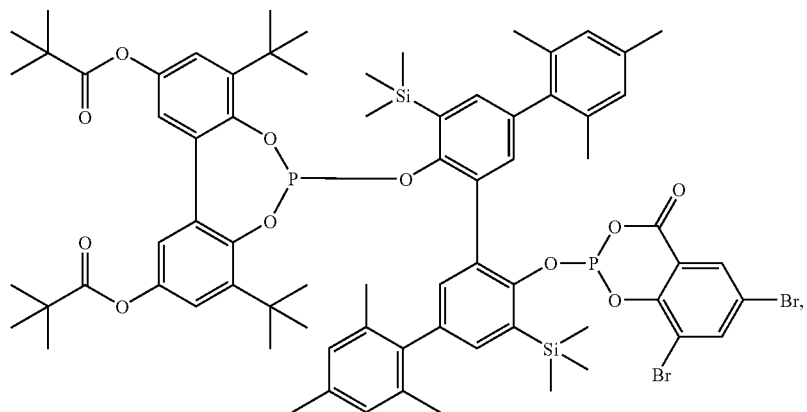

-continued
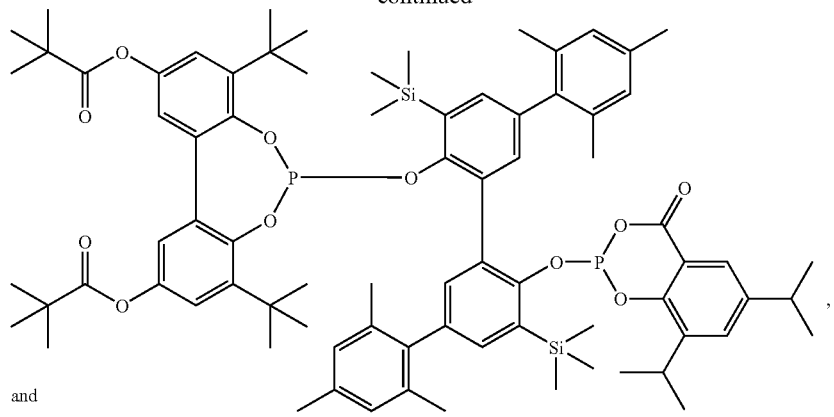
and
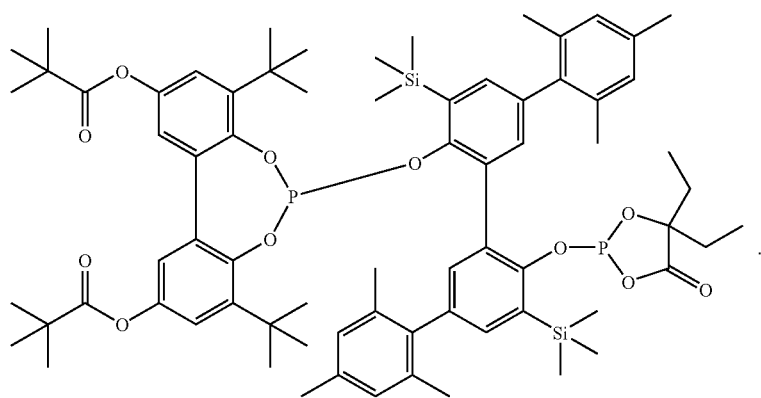
39. The solution of claim 19 wherein free and bonded phosoxophite ligands are independently selected from the group consisting of:
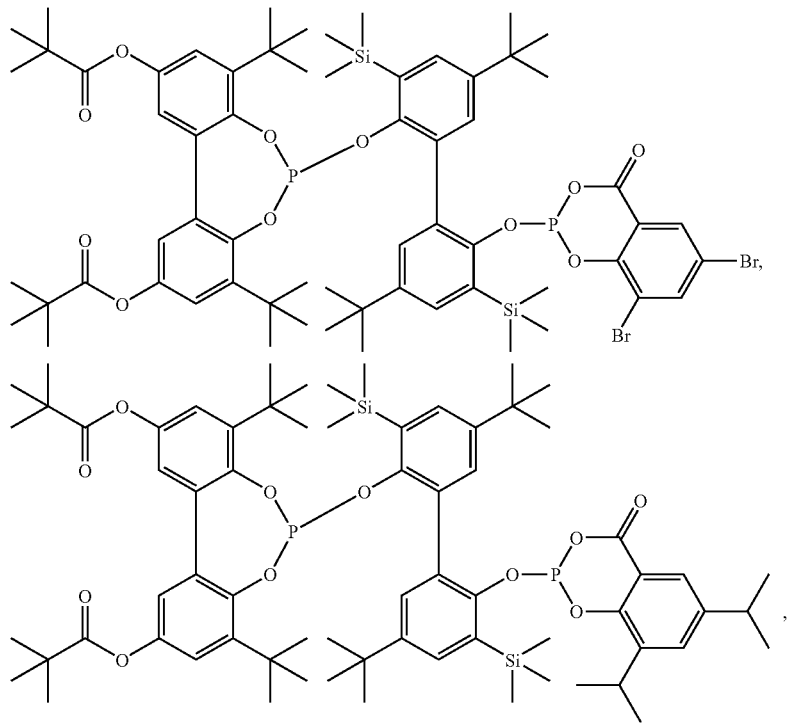

-continued
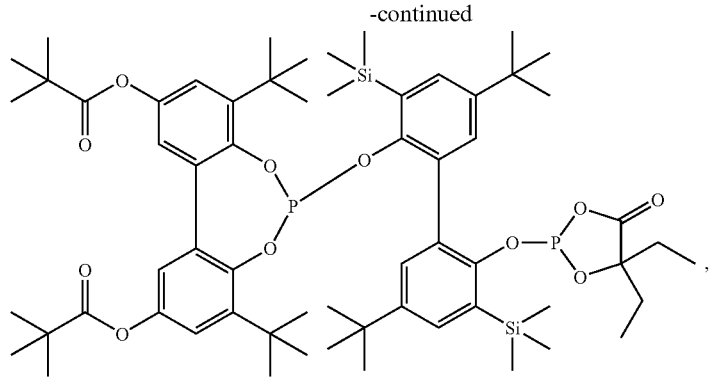
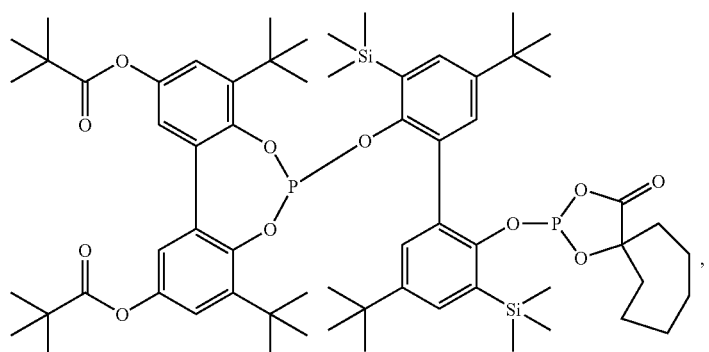
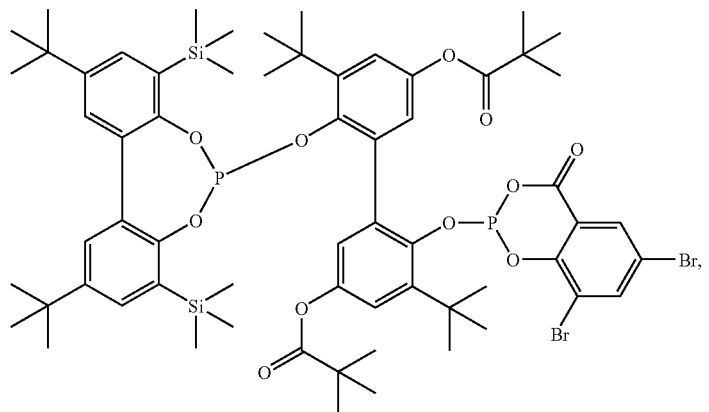
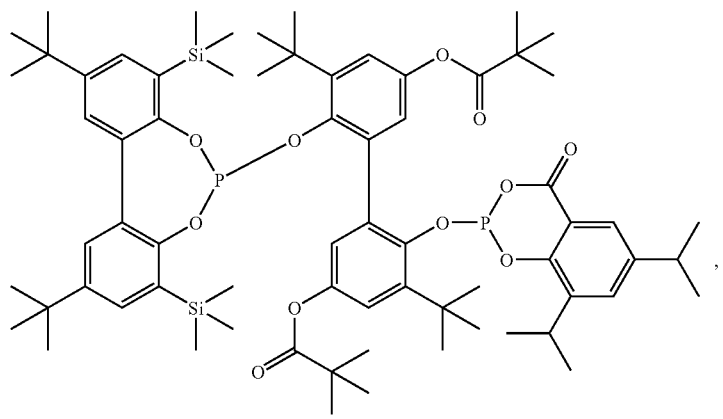

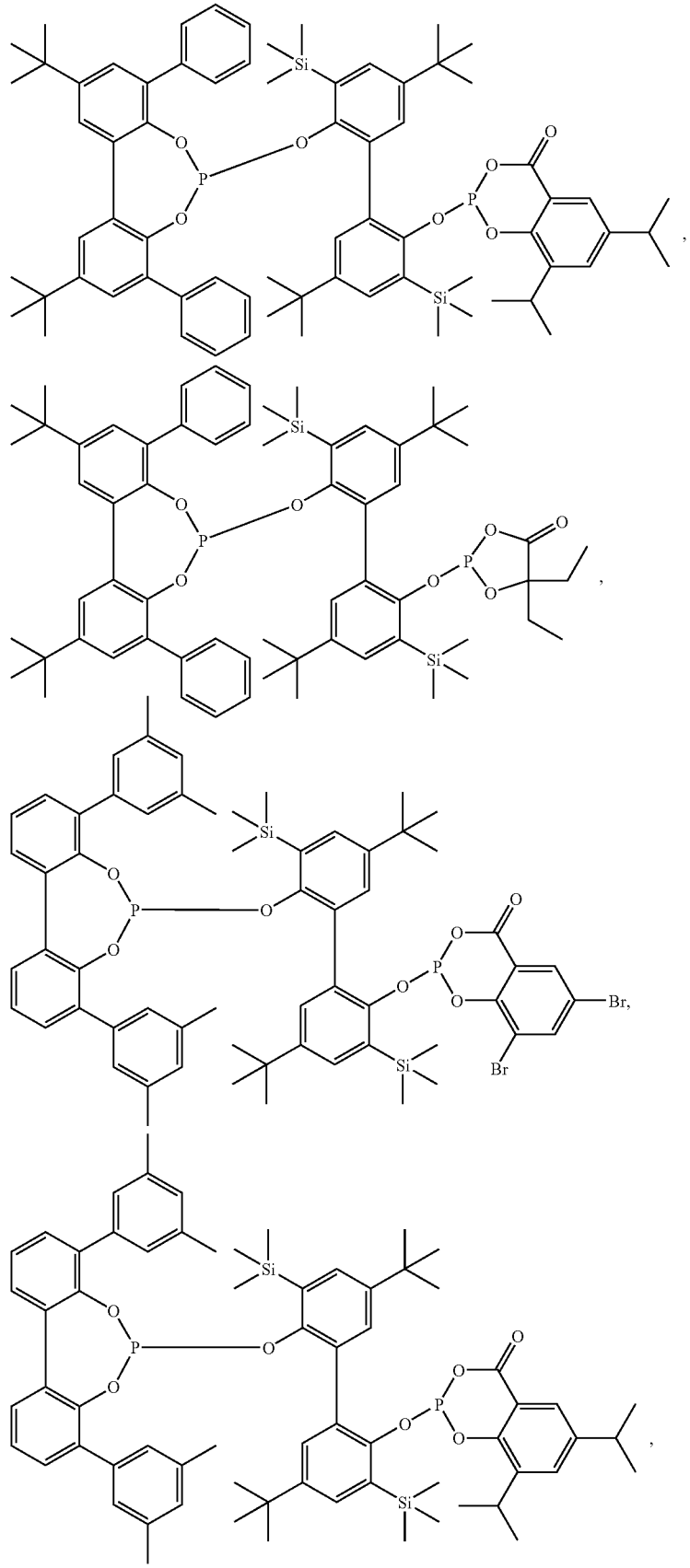

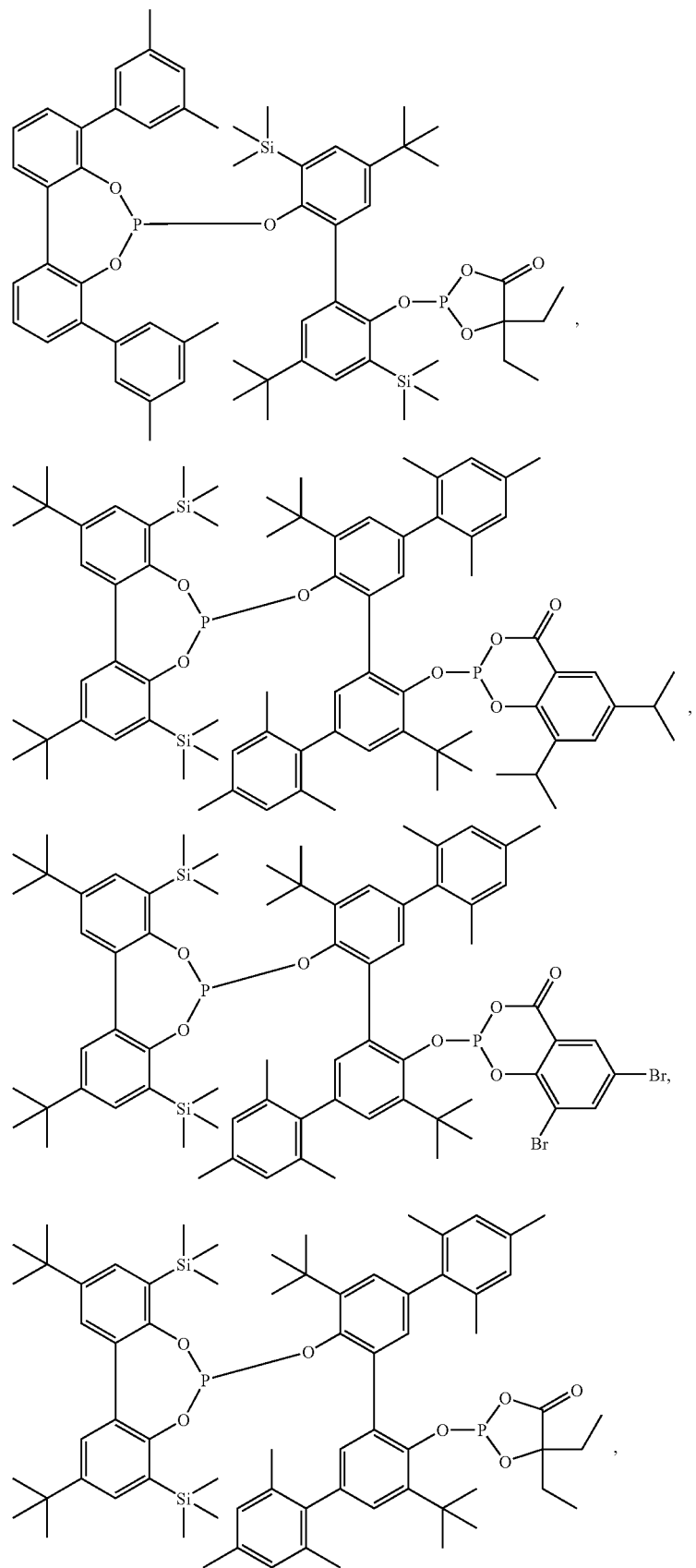

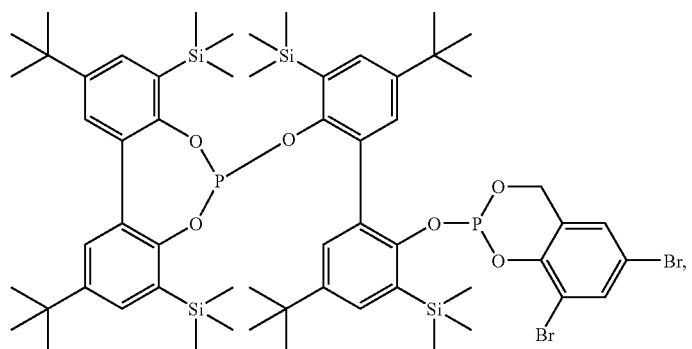
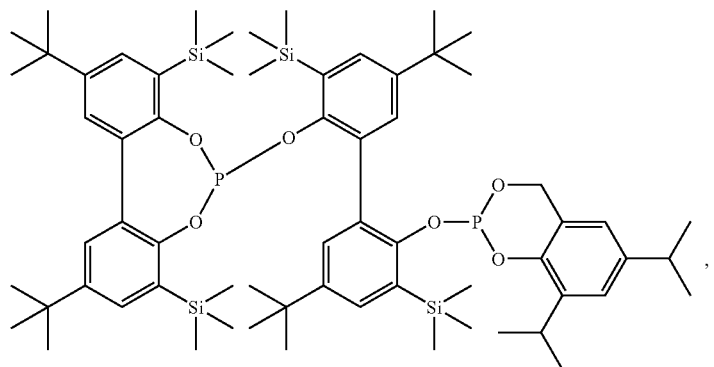
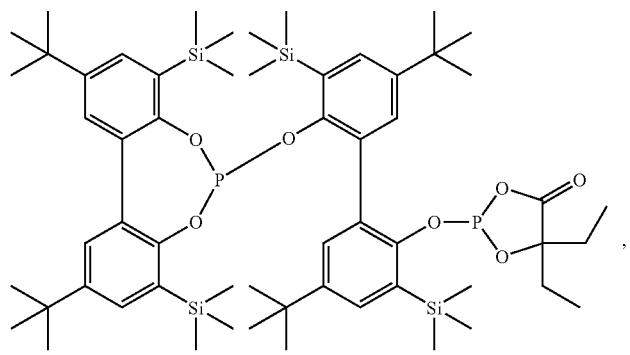
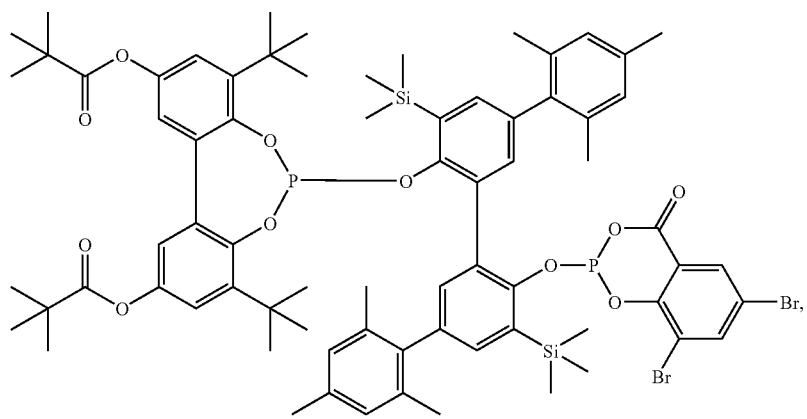

-continued
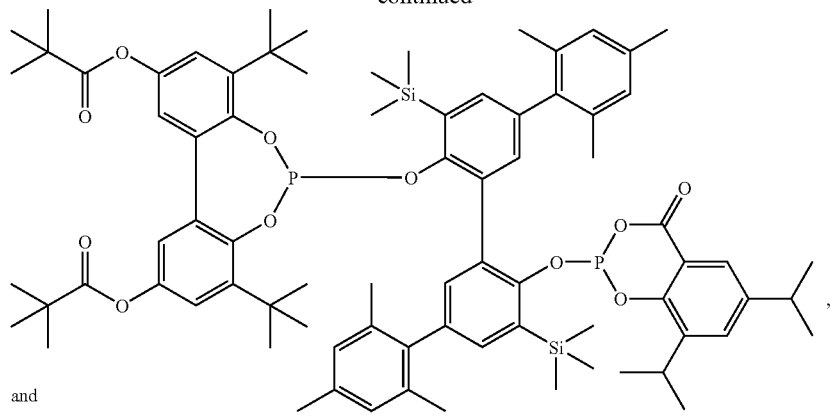
and
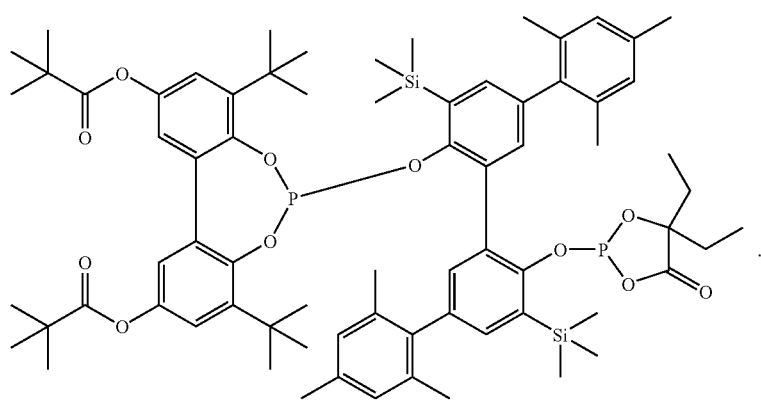
40. The carbonylation process of claim 22 wherein the free and bonded phosoxophite ligands are each independently selected from the group consisting of:
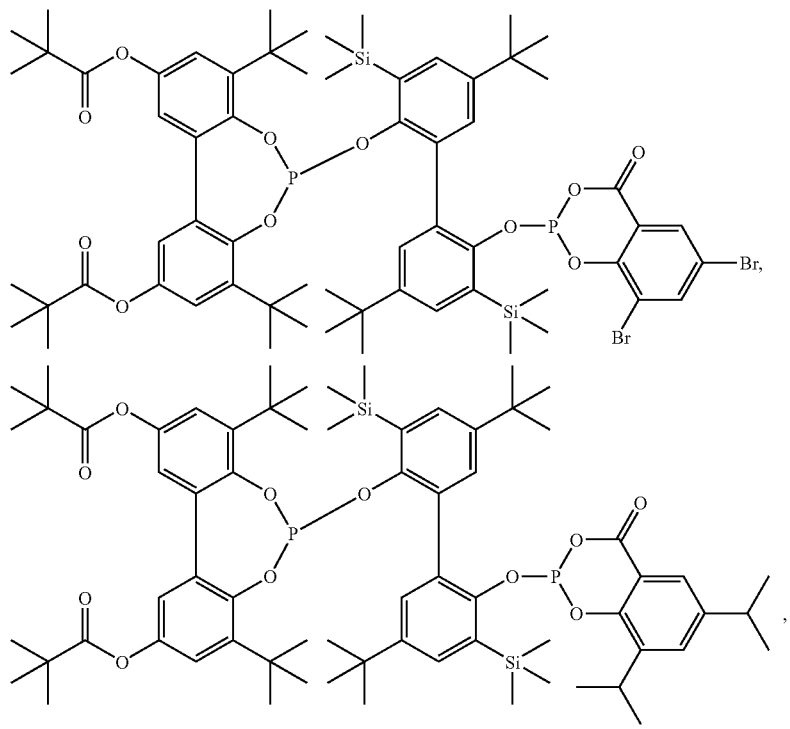

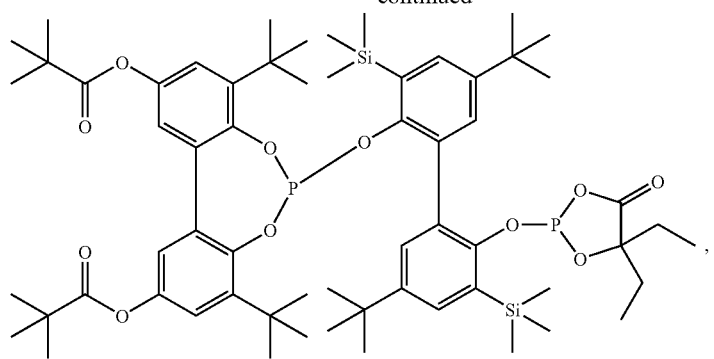
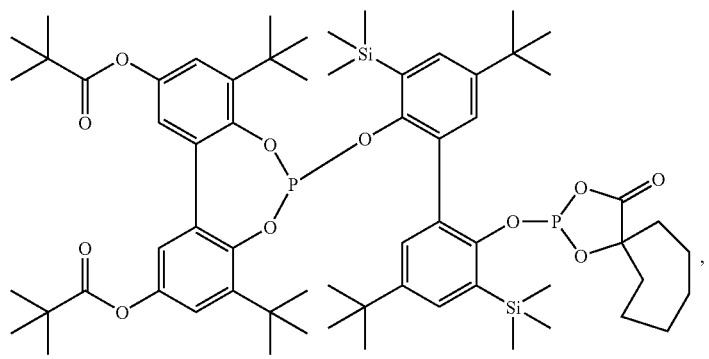
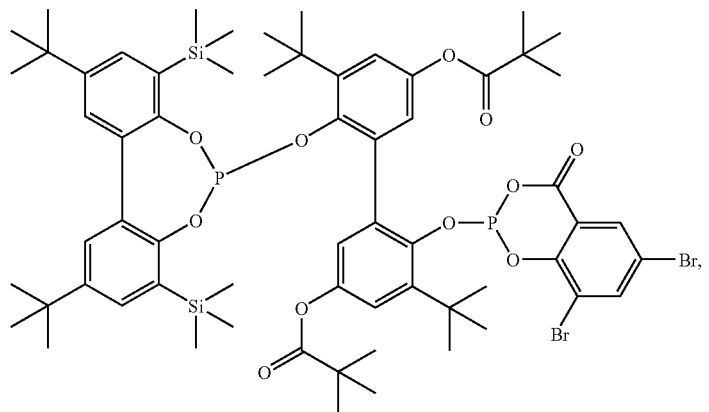
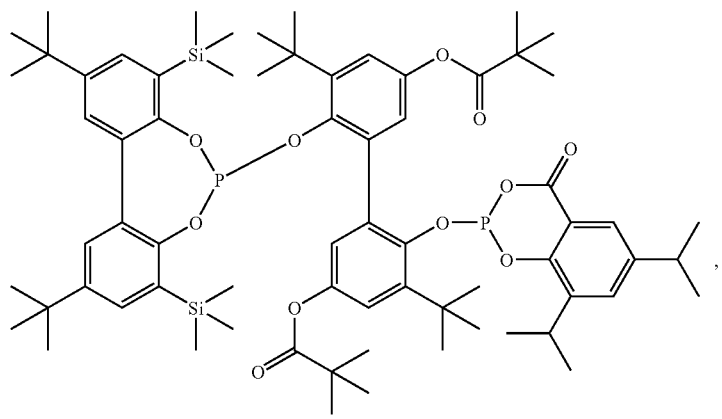

-continued
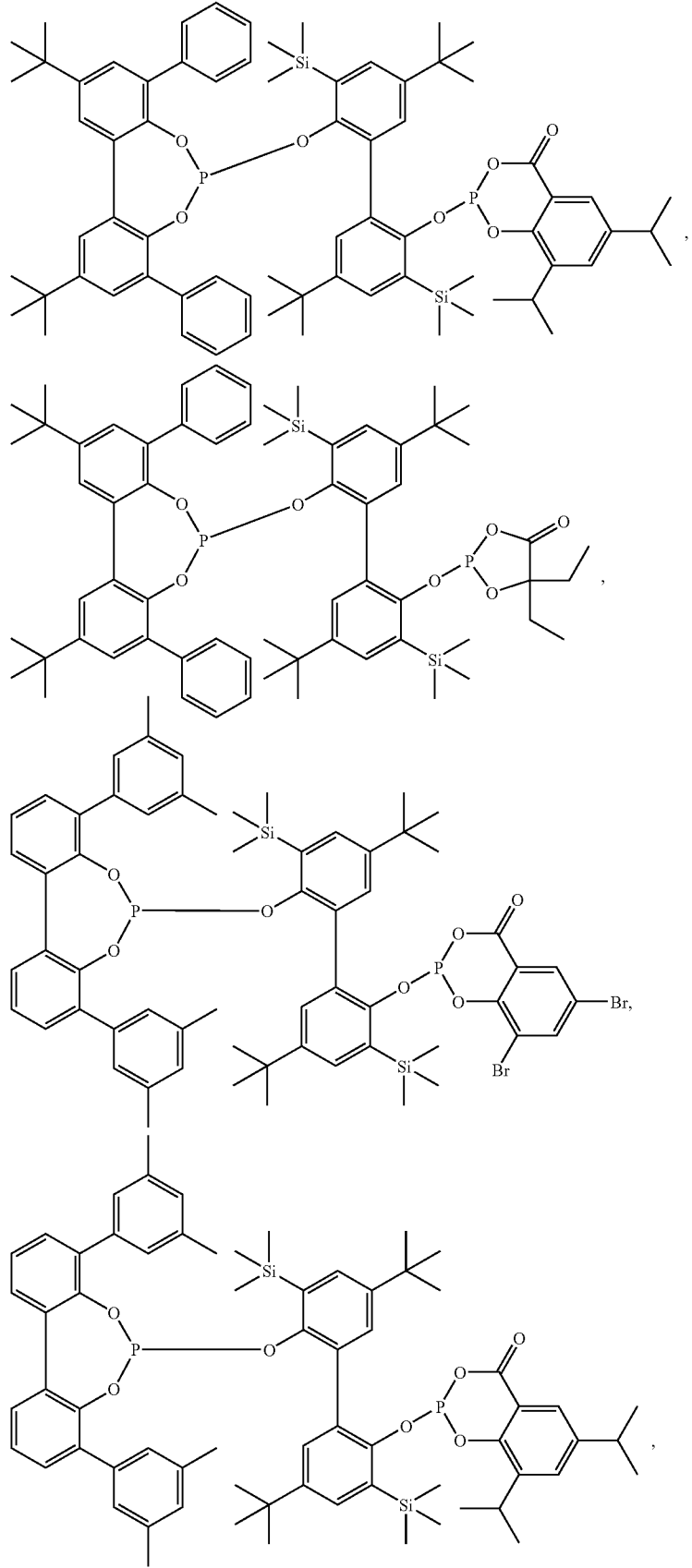

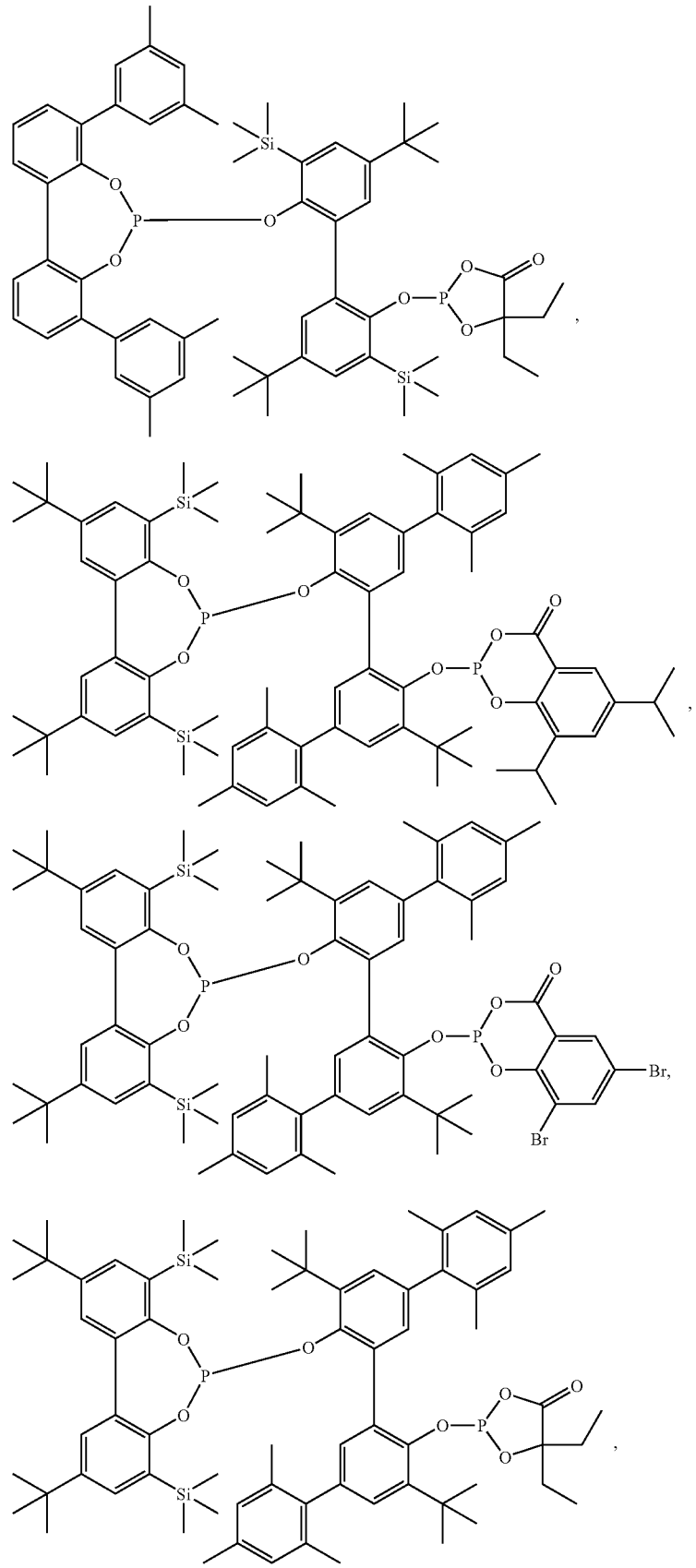

-continued
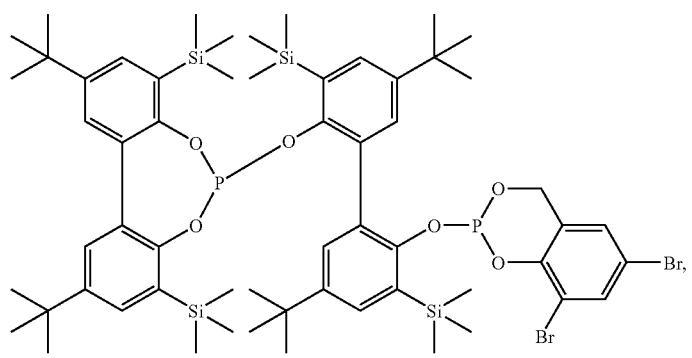
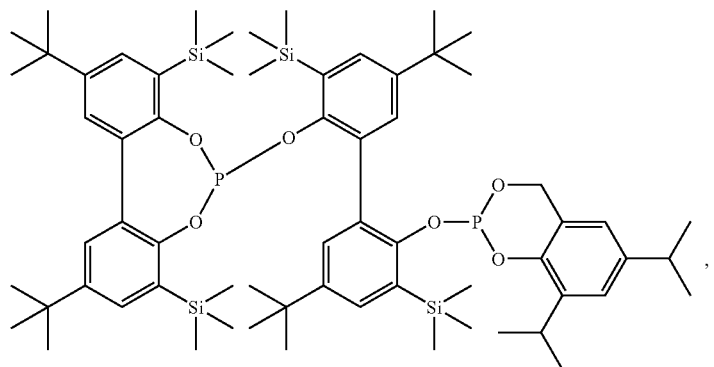
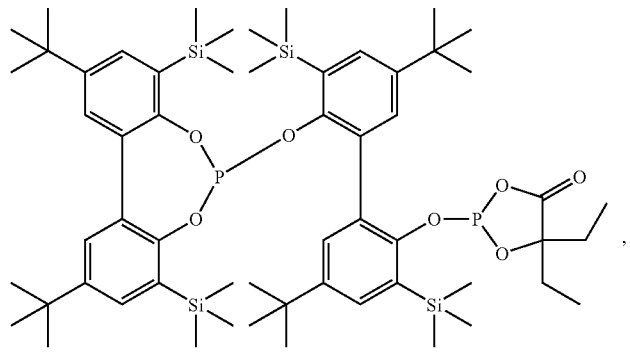
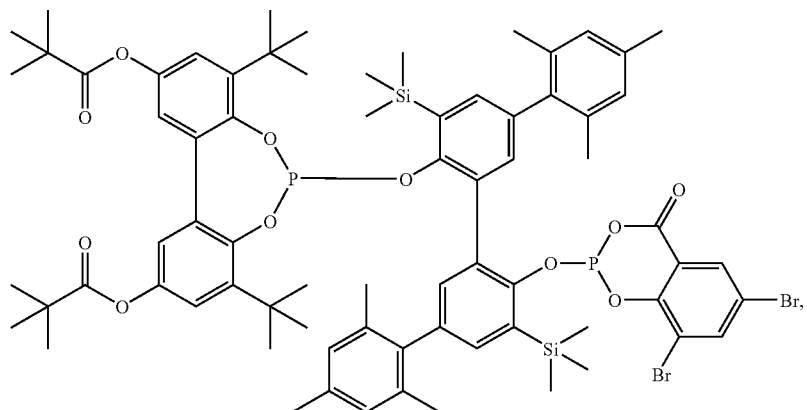

-continued
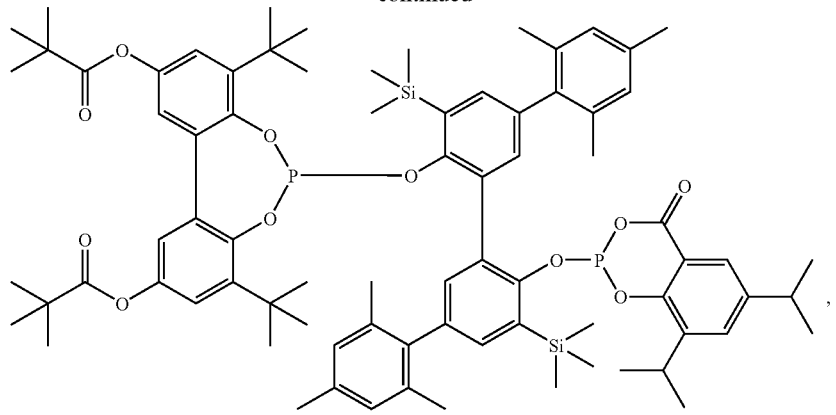
and
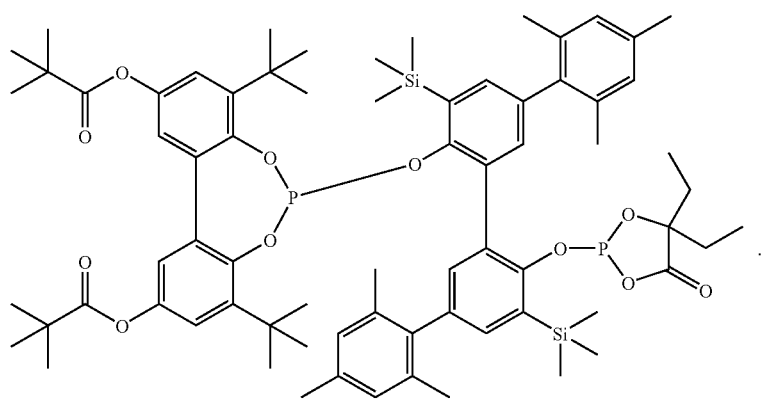
* * * * *